United States Patent [19]

Martinis et al.

[11] Patent Number: 5,798,240
[45] Date of Patent: Aug. 25, 1998

[54] RECOMBINANT MYCOBACTERIAL METHIONYL-TRNA SYNTHETASE GENES AND METHODS OF USE THEREFORE

[75] Inventors: Susan A. Martinis, Newton; Mandana Sassanfar, Dedham, both of Mass.; Sunghoon Kim, Seoul, Rep. of Korea; Sang Ho Lee, Boston; Paul R. Schimmel, Cambridge, both of Mass.

[73] Assignee: Cubist Pharmaceuticals, Inc., Cambridge, Mass.

[21] Appl. No.: 584,226

[22] Filed: Jan. 11, 1996

Related U.S. Application Data

[62] Division of Ser. No. 305,766, Sep. 13, 1994, abandoned.
[51] Int. Cl.$^6$ .............................. C12N 9/00; C12N 15/00; C12N 1/20; C07H 21/04
[52] U.S. Cl. .................. 435/183; 435/252.3; 435/320.1; 435/863; 435/69.7; 536/23.2; 536/23.4
[58] Field of Search .................................. 435/69.7, 183, 435/252.3, 320.1, 863; 536/23.2, 23.4

[56] References Cited

U.S. PATENT DOCUMENTS

| | | | |
|---|---|---|---|
| 4,713,337 | 12/1987 | Jasin et al. | 435/172.3 |
| 4,788,148 | 11/1988 | Nilsson et al. | 435/320 |
| 4,952,501 | 8/1990 | Jasin et al. | 435/69.2 |
| 4,963,487 | 10/1990 | Schimmel et al. | 435/172.3 |
| 5,358,862 | 10/1994 | Hardesty et al. | 435/172.3 |
| 5,370,995 | 12/1994 | Hennecke et al. | 435/69.1 |
| 5,534,421 | 7/1996 | Livshits et al. | 435/116 |

FOREIGN PATENT DOCUMENTS

WO 95/09927   4/1995   WIPO.

OTHER PUBLICATIONS

Kumazawa, Yoshinori, et al., "Unilateral Aminoacylation Specificity between Bovine Mitochondria and Eubacteria," *J. Biochem.*, 109:421–427 (1991).

Cusack, Stephen, et al., "A Second Class of Synthetase Structure Revealed by X–ray Analysis of *Escherichia coli* Seryl–tRNA Synthetase at 2.5 Å," *Nature*, 347:249–255 (Sep. 1990).

Nichols, Ralph C., et al., "Human Isoleucyl–tRNA Synthetase:Sequence of the cDNA, Alternative mRNA Splicing, and the Characteristics of an Unusually Long C–terminal Extension," *Gene*, 155:299–304 (1995).

Lazard, Myriam, et al., "Purification and Characterization of the Isoleucyl–tRNA Synthetase Component From the High Molecular Weight Complex of Sheep Liver: A Hydophobic Metalloprotein." *Biochemistry*, 24:5099–5106 (1985).

Natarajan, V., and Gopinathan, K.P., "Mechanism of Aminoacylation of tRNA: Influence of Spermine on the Kinetics of Aminoacyl–tRNA Synthesis by Isoleucyl– and Valyl–tRNA Synthetases from *Mycobacterium smegmatis*," *Biochimica et Biophysica Acta.* 654:94–101 (1981).

Hou, Y–M., et al., "Sequence Determination and Modeling of Structural Motifs for the Smallest Monomeric Aminoacyl–tRNA Synthetase," *Proc. Natl. Acad. Sci. USA*, 88:976–980 (1991).

Heck, J.D., and Hatfield, G.W., "Valyl–tRNA Synthetase Gene of *Escherichia coli* K12: Primary Structure and Homology Within a Family of Aminoacyl–tRNA Synthetases, " *The Journal of Biological Chemistry*, 263 (2) :868–877 (1988).

Natarajan, V., and Gopinathan, K.P., "Stimulation of Valyl–and Isoleucyl–tRNA Synthetase Reactions by Polyamines, " *J. Biosci.*, 1(4) :357–367 (1979).

Deobagkar, D.N., and Gopinathan, K.P., "Influence of Monovalent Cations on Aminoacylation of Transfer RNA," *Indian Journal of Biochemistry & Biophysics*, 13:24–30 (Mar. 1976).

Natarajan, V., and Gopinathan, K.P., "Purification & Properties of Valyl–tRNA Synthetase from *Mycobacterium tuberculosis* $H_{37}R_v$," *Indian Journal of Biochemistry & Biophysics*, 17:330–334 (Oct. 1980).

Edwards, H., et al., "An *E. coli* Aminoacyl–tRNA Synthetase Can Substitute for Yeast Mitochondrial Enzyme Function In Vivo." *Cell* 51:643–649, Nov. 20, 1987.

Racher, K.I., et al., "Expression and Characterization of a Recombinant Yeast Isoleucyl–tRNA Synthetase," *The Journal of Biological Chemistry* 266 (26):17158–17164, Sep. 15, 1991.

(List continued on next page.)

*Primary Examiner*—Robert A. Wax
*Assistant Examiner*—Lisa J. Hobbs
*Attorney, Agent, or Firm*—Hamilton, Brook, Smith & Reynolds, P.C.

[57] ABSTRACT

Isolated and/or recombinant nucleic acids encoding mycobacterial methionyl-tRNA synthetase have been characterized. Recombinant DNA constructs and vectors having a sequence which encodes mycobacterial methionyl-tRNA synthetase have been made, and can be used for the construction of tester strains as well as for the production of isolated and/or recombinant methionyl-tRNA synthetases. These enzymes or portions thereof are useful in the biochemical separation of methionine and quantification of methionine or ATP, and for producing antibodies useful in the purification and study of the enzyme, for example. Host cells and methods useful for producing recombinant mycobacterial methionyl-tRNA synthetases are described, as are tester strains, which are cells engineered to rely on the function of the tRNA synthetase encoded by an introduced cloned gene. Tester strains can be used to identify inhibitors of the essential tRNA synthetase enzyme encoded by the introduced cloned gene, and thus provide a means to assess the antimicrobial effect and specificity of the inhibitor without employing slow-growing, pathogenic strains of mycobacteria, such as *Mycobacterium tuberculosis*.

62 Claims, 1 Drawing Sheet

OTHER PUBLICATIONS von der Haar, F. et al., "Target Directed Drug Synthesis: The Aminoacyl–tRNA Synthetase as Possible Targets," *Angew. Chem. Int. Ed. Engl.*, 20 (3) :217–223 (1981).

Chalker, A.F., et al., "Analysis and Toxic Overexpression in *Escherichia coli* of a Staphylococcal Gene Encoding Isoleucyl–tRNA Synthetase," *Gene*, 141:103–108 (1994).

Hughes, J. and Mellows, G., "Interaction of Pseudomonic Acid A with *Escherichia coli* B Isoleucyl–tRNA Synthetase," *Biochem J.*, 191:209–219 (1980).

Weygand–Duraševič, I., et al., "Yeast Seryl–tRNA Synthetase Expressed in *Escherichia coli* Recognizes Bacterial Serine– Specific tRNAs in vivo," *Eur. J. Biochem.* 214:869–877 (1993).

Walter, R. D. and Kuhlow, F., "Parasite–Specific Interaction of N–|4–(4' Nitroanilino)–Phenyl]–S–(β–Carboxyethyl)– Dithiocarbamic Acid–Ester with Arginyl–tRNA–Synthetase from *Dirofilaria immitis*," *Trop. Med. Parasit.* 36:230–232 (1985).

Meinnel, T., et al., "Aminoacyl–tRNA Synthetases: Occurrence, Structure, and Function," *In tRNA: Structure, Biosynthesis, and Function*, Söll, D. and RajBhandary, U., eds. (Washington, DC: American Society for Microbiology), pp. 251–300 (1995).

Webster, T., et al., "Specific Sequence Homology and Three–Dimensional Structure of an Aminoacyl Transfer RNA Synthetase," *Science* 226:1315–1317, Dec. 1984.

Englisch, U., et al., "Structure of the Yeast Isoleucyl–tRNA Synthetase Gene (ILS1)," *Biol. Chem. Hoppe–Seyler* 368:971–979, Aug. 1987.

Martindale, D.W., et al., "Isolation and complete sequence of the yeast isoleucyl–tRNA synthetase gene (ILS1)," *Current Genetics* 15:99–106 (1989).

Jenal, U., et al., "Isoleucyl–tRNA Synthetase of *Methanobacterium thermautotrophicum* Marburg," *The Journal of Biological Chemistry* 266 (16) :10570–10577, Jun. 5, 1991.

Csank, C., et al., Isoleucyl–tRNA Synthetase from the Ciliated Protozoan *Tetrahymena thermophila, The Journal of Biological Chemistry* 267(7) :4592–4599, Mar. 5, 1992.

Shiba, K., et al., "Human cytoplasmic isoleucyl–tRNA synthetase: Selective divergence of the anticodon–binding domain and acquisition of a new structural unit," *Proc. Natl. Acad. Sci. USA*, 91:7435–7439, 1994.

Shepard, A., et al., "RNA Binding Determinant in Some Class I tRNA Synthetases Identified by Alignment–Guided Mutagenesis," *Proc. Natl. Acad. Sci. USA*, 89:9964–9968 (1992).

Shiba, K. and Shimmel, P., "Functional Assembly of a Randomly Cleaved Protein," *Proc. Natl. Acad. Sci. USA*, 89:1880–1884 (1992).

Iaccarino, M. and Berg, P., "Isoleucine Auxotrophy as a Consequence of a Mutationally Altered Isoleucyl–Transfer Ribonucleic Acid Synthetase," *J. Bacteriol.*, 105:527–537 (1970).

Kim, S., et al., "Diversified Sequences of Peptide Epitope for Same–RNA Recognition," *Proc. Natl. Acad. Sci. USA*, 90:10046–10050 (1993).

Archibold, E.R., and Williams, L.S., "Regulation of Methionyl–Transfer Ribonucleic Acid Synthetase Formation in *Escherichia coli* and *Salmonella typhimurium*," *Journal of Bacteriology*, 114(3) :1007–1013 (1973).

Tzagoloff, A., et al., "Characterization of MSM1, the Structural Gene for Yeast Mitochondrial Methionyl–tRNA Synthetase," *Eur. J. Biochem.*, 179:365–371 (1989).

Dardel, F., et al., "Molecular Cloning and Primary Structure of the *Escherichia coli* Methionyl–tRNA Synthetase Gene," *Journal of Bacteriology*, 160(3) :1115–1122 (1984).

Nureki, O., et al., "Methionyl–tRNA Synthetase Gene From an Extreme Thermophile, *Thermus thermophilus* HB8," *The Journal of Biological Chemistry*, 266(5) :3268–3277 (1991).

Mechulam, Y., et al., "Methionyl–tRNA Synthetase from *Bacillus stearothermophilus*: Structural and Functional Identities with the *Escherichia coli* Enzyme," *Nucleic Acids Research*, 19(13) :3673–3681 (1991).

Walter, P., et al., "Primary Structure of the *Saccharomyces cerevisiae* Gene for Methionyl–tRNA Synthetase," *Proc. Natl. Acad. Sci. USA*, 80:2437–2441 (1983).

Fasiolo, F., et al., "Cytoplasmic Methionyl–tRNA Synthetase from Bakers' Yeast," *The Journal of Biological Chemistry*, 260 (29) :15571–15576 (1985).

Jasin, M. and Schimmel, P., "Deletion of an Essential Gene in *Escherichia coli* by Site–Specific Recombination with Linear DNA Fragments," *J. Bacteriol.* 159(2) :783–786 (1984).

Edwards, H. and Schimmel, P., "A Bacterial Amber Suppressor in *Saccharomyces cerevisiae* Is Selectively Recognized by a Bacterial Aminoacyl–tRNA Synthetase," *Molecular and Cellular Biology*, 10(4) :1633–1641 (1990).

Shiba, K., et al., "Isolation of Higher Eukaryote Aminoacyl–tRNA Synthetase Genes by an Alignment–Guided Cross–Species PCR: Application to Human Isoleucine tRNA Synthetase," [*From Programme and Abstracts*, p. F.46], 15th International tRNA Workshop, Société Francaise de Biochimie et Biologie Moléculaire, Cap d'Agde, France, May 30–Jun. 4 (1993), Abstract No. 364.

Printout of a computer record of parts of a poster presented at Cap d'Agde, France, May 30–Jun. 4, 1993, 15th International tRNA Workshop, Société Francaise de Biochimie et Biologie Moléculaire.

Sequence of Human Isoleucyl–tRNA Synthetase Gene, GenBank Name: HSU04953, Accession: U04953, National Center for Biotechnology Information Seq ID: 450850. Entered by Nichols, R.C., et al. First Available: Jan. 13, 1994; Updated: Jan. 26, 1994.

Hughes, J., et al., "Inhibition of Isoleucyl–Transfer Ribonucleic Acid Synthetase in *Escherichia coli* by Pseudomonic Acid," *Biochem. J.* 176:305–318 (1978).

Härtlein, M. and Madern, D., "Molecular Cloning and Nucleotide Sequence of the Gene for *Escherichia coli* Leucyl–tRNA Synthetase," *Nucleic Acids Research* 15(24) :10199–10210 (1987).

Chow, C. M., et al., "Nuclear Gene for Mitochondrial Leucyl–tRNA Synthetase of *Neurospora crassa*: Isolation, Sequence Chromosomal Mapping, and Evidence that the leu–5 Locus Specifies Structural Information," *Mol. and Cell. Biol.* 9(11) :4631–4644 (1989).

Chow, C. M., and RajBhandary, U. L., "Regulation of the Nuclear Genes Encoding the Cytoplasmic and Mitochondrial Leucyl–tRNA Synthetases of *Neurospora crassa*," *Molecular and Cellular Biology* 9(11) :4645–4652 (1989).

Hohmann, S. and Thevelein, J. M., "The Cell Division Cycle Gene CDC60 Encodes Cytosolic Leucyl–tRNA Synthetase in *Saccharomyces cerevisiae*," *Gene* 120:43–49 (1992).

Tzagoloff, A., et al., "Homology of Yeast Mitochondrial Leucyl–tRNA Synthetase and Isoleucyl– and Methionyl–tRNA Synthetases of *Escherichia coli*," *The Journal of Biological Chemistry*, 263 (2) :850–856 (1988).

Low, B., et al., "Isolation and Partial Characterization of Temperature–Sensitive *Escherichia coli* Mutants with Altered Leucyl–and Seryl–Transfer Ribonucleic Acid Synthetases," *Journal of Bacteriology*, 108(2) :742–750 (1971).

Vander Horn, P. B., and Zahler, S. A., "Cloning and Nucleotide Sequence of the Leucyl–tRNA Synthetase Gene of *Bacillus subtilis*," *Journal of Bacteriology*, 174(12) :3928–3935 (1992).

Herbert, C. J., et al., "The NAM2 Proteins from *S. cerevisiae* and *S. douglasii* are Mitochondrial Leucyl–tRNA Synthetases, and are Involved in mRNA Splicing," *The EMBO Journal*, 7(2) :473–483 (1988).

Fujinaga, M., et al., "Refined Crystal Structure of the Seryl–tRNA Synthetase from *Thermus thermophilus* at 2.5 ÅResolution," *J. Mol. Biol.* 234:222–233 (1993).

Lunel, C., et al., "A Seryl–tRNA Synthetase Gene is Coamplified with the Adenylate Deaminase 2 Gene in Coformycin Resistant, Chinese Hamster Fibroblasts," *Nucleic Acids Research*, 20(10) :2597 (1992).

Weygand–Duraševič, I., et al., "Cloning and Characterization of the Gene Coding for Cytoplasmic Seryl–tRNA Synthetase from *Saccharomyces cerevisiae*," *Nucleic Acids Research*, 15(5) :1887–1904 (1987).

Clarke, S. J., et al., "Isolation and Characterization of a Regulatory Mutant of an Aminoacyl–Transfer Ribonucleic Acid Synthetase in *Escherichia coli* K–12, " *Journal of Bacteriology*, 113 (3) :1096–1103 (1973).

Miseta, A., et al., "Mammalian Seryl–tRNA Synthetase Associates with MRNA in Vivo and Has Homology to Elongation Factor 1α," *The Journal of Biological Chemistry*, 266(29) :19158–19161 (1991).

Jones, M. D., et al., "Natural Variation of Tyrosyl–tRNA Synthetase and Comparison with Engineered Mutants," *Biochemistry*, 25:1887–1891 (1986).

Barker, D. G., et al., "The Tyrosyl–tRNA Synthetase from *Escherichia coli*," *FEBS Letters*, 150(2) :419–423 (1982).

Chow, C. M., and RajBhandary, U. L., "*Saccharomyces cerevisiae* Cytoplasmic Tyrosyl–tRNA Synthetase Gene," *The Journal of Biological Chemistry*, 268(17) :12855–12863 (1993).

Salazar, O., et al., "*Thiobacillus ferrooxidans* Tyrosyl–tRNA Synthetase Functions In Vivo in *Escherichia coli*" *Journal of Bacteriology*, 176(14) :4409–4415 (1994).

Sequence of *Mycobacterium leprae* cosmid L247 as in database on Sep. 13, 1994. GenBank Accession No. U00021. Submitted by Robison, K., Nov. 1, 1993 (22 pages).

Henkin, T. M., et al., "Analysis of the *Bacillus subtilis* tyrS Gene: Conservation of a Regulatory Sequence in Multiple tRNA Synthetase Genes," *Journal of Bacteriology*, 174(4) :1299–1306 (1992).

Akins, R. A., and Lambowitz, A. M., "A Protein Required for Splicing Group I Introns in Neurospora Mitochondria Is Mitochondrial Tyrosyl–tRNA Synthetase or a Derivative Thereof," *Cell*, 50:331–345 (1987).

Winter, G., et al., "The Amino Acid Sequence of the Tyrosyl–tRNA Synthetase from *Bacillus stearothermophilus*," *Eur. J. Biochem.*, 132:383–387 (1983).

Schlesinger, S., and Nester, E. W., "Mutants of *Escherichia coli* with an Altered Tyrosyl–Transfer Ribonucleic Acid Synthetase," *Journal of Bacteriology*, 100(1) :167–175 (1969).

Glaser, P., et al., "A Gene Encoding a Tyrosine tRNA Synthetase is Located Near sacS in *Bacillus subtilis*," *DNA Sequence*, 1:251–261 (1991).

Gopinathan, K. P., "Molecular Biology of Mycobacteria and Mycobacteriophages," *J. Indian Inst. Sci.*, 73:31–45 (1993).

Predich, M., et al., "Characterization of RNA polymerase and two sigma–factor genes from *Mycobacterium smegmatis*", *Molecular Microbiol.*, 15(2) :355–366 (1995).

Laske, R., et al., "Untersuchungen zum Wirkmechanismus antimykobakterieller Benzylamine," *Arch. Pharm. (Weinheim)*, 322:297–299 (1989).

Deobagkar, D. N., and Gopinathan, K. P., "Studies on Transfer RNA from Mycobacteria," *Can. J. Microbiol.*, 24:693–702 (1978).

Deobagkar, D. N., and Gopinathan, K. P., "Two Forms of Methionyl–Transfer RNA Synthetase from Mycobacterium," *Biochemical and Biophysical Research Communications*, 71(4) :939–951 (1976).

Sela, S., et al., "Identification of *Mycobacterium leprae* Antigens from a Cosmid Library: Characterization of a 15–Kilodalton Antigen That Is Recognized by Both the Humoral and Cellular Immune Systems in Leprosy Patients," *Infection and Immunity*, 59(11) :4117–4124 (1991).

MCS = multiple cloning site

MCS = multiple cloning site

5,798,240

RECOMBINANT MYCOBACTERIAL METHIONYL-TRNA SYNTHETASE GENES AND METHODS OF USE THEREFORE

This application is a division of application Ser. No 08/305,766 filed Sep. 13, 1994, now abandoned which is incorporated herein by reference in its entirety.

BACKGROUND OF THE INVENTION

Mycobacteria are slow-growing aerobic bacteria characterized by their surface glycolipids, and by the high G-C content of their DNA (>63%). Organisms of the genus Mycobacterium include more than 30 well-characterized members and many that are as yet unclassified. Most are not pathogenic for humans, but among the mycobacteria are the etiologic agents for leprosy (*M. leprae*) and for tuberculosis (*M. tuberculosis*), the leading cause of death in the world from an infectious disease (Bloom, B. R. and C. J. L. Murray, *Science*, 257:1055–1064 (1992)).

It has been estimated that as much as one-third of the population of the world is infected with *M. tuberculosis*, and that tuberculosis (TB) is responsible for one in four avoidable adult deaths in developing countries (Murray, C. J. L. et al., 1993, In: *Disease Control Priorities in Developing Countries*, D. T. Jamison et al., Eds. (Oxford Univ. Press: New York) pp. 233–259). Since the 1980s the number of new cases of TB infections has steadily increased both in the US and in Europe. Individuals infected with the human immunodeficiency virus (HIV) are particularly susceptible to infection with *M. tuberculosis*, a growing problem that threatens the control of the spread of tuberculosis.

Infection caused by drug-sensitive strains of *M. tuberculosis* has been successfully treated by using a combination of isoniazid, rifampicin and pyrazinamide. However, in cities worldwide, the emergence of multidrug resistant isolates of *M. tuberculosis* is becoming alarming. The fatality rate for drug-resistant TB is 50%. According to the World Health Organization, almost 20% of the isolates tested in New York City in 1992 were resistant to both isoniazid and rifampicin.

It would be a great advantage in the control of diseases caused by the Mycobacteria to expand the number of target molecules whose function could be inhibited by antibiotic agents.

SUMMARY OF THE INVENTION

The invention relates to isolated and/or recombinant nucleic acids which encode methionyl-tRNA (Met tRNA) synthetases (MetRSs) of mycobacterial origin. The invention also relates to recombinant DNA constructs and vectors containing DNA having a sequence which encodes a methionyl-tRNA synthetase of mycobacterial origin, or portions of the enzyme. These nucleic acids and DNA constructs can be used to produce recombinant methionyl-tRNA synthetase of mycobacterial origin.

A further embodiment of the invention is antisense nucleic acid which can hybridize to the nucleic acid which encodes the methionyl-tRNA synthetase of mycobacteria. In cells, antisense nucleic acid can inhibit the function of an RNA which encodes the methionyl-tRNA synthetase of mycobacteria.

The invention also relates to proteins or polypeptides, referred to herein as isolated, recombinant mycobacterial methionyl-tRNA synthetases. These enzymes are useful in biochemical separation of methionine and quantitations of methionine and ATP. Antibodies which bind to these enzymes can be made and can be used in the purification and study of the enzyme.

The recombinant mycobacterial methionyl-tRNA synthetases can be produced in host cells using cells and methods described herein. Tester strains, which are cells engineered to rely on the function of the tRNA synthetase encoded by an introduced cloned gene, are also an embodiment of the invention. Tester strains can be used to test the effectiveness of drug candidates in the inhibition of the essential tRNA synthetase enzyme encoded by the introduced cloned gene. In this way, potential inhibitors can be screened for antimicrobial or antibiotic effects, without having to employ slow-growing, pathogenic strains of mycobacteria.

DETAILED DESCRIPTION OF THE INVENTION

Figure 1:
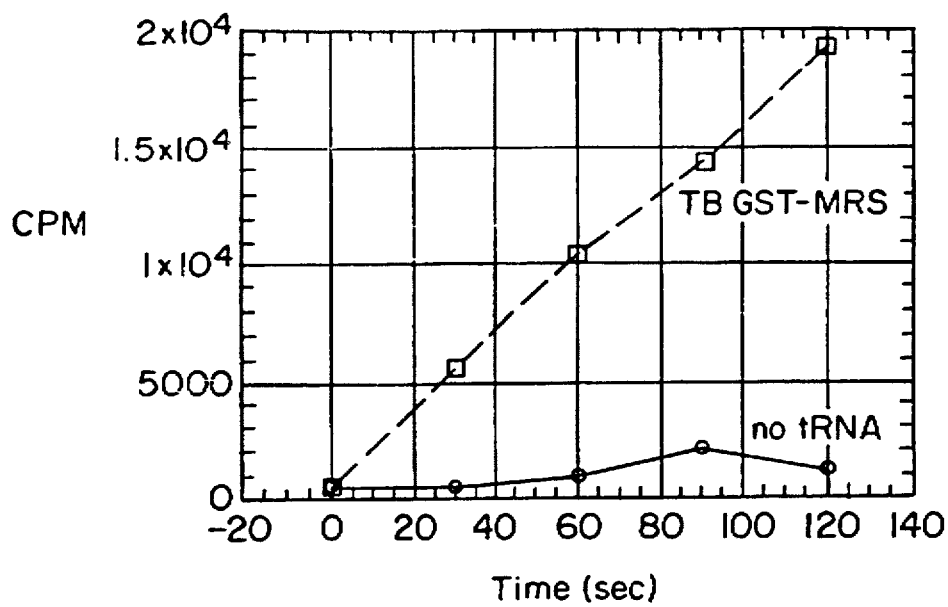
FIG. 1 is a graph illustrating the results of an experiment in which the aminoacylation activity of the *M. tuberculosis* GST-Met tRNA synthetase, using *E. coli* tRNA$^{fMet}$ as a substrate, was determined (Example 5). □, *M. tuberculosis* GST Met tRNA synthetase; O, no tRNA control.

The aminoacyl-tRNA synthetases are enzymes with the common general function of catalyzing the following reaction:

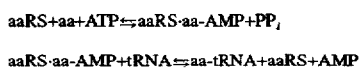

(aaRS=aminoacyl-tRNA synthetase; aa=amino acid; ATP=adenosine 5'-triphosphate; AMP=adenosine 5'-monophosphate; PP$_i$=inorganic pyrophosphate) The second (aminoacylation) step is often referred to as "charging" the tRNA.

Generally, in each bacterial organism, there are 20 different aaRSs, one specific for each amino acid. For each amino acid, eucaryotic organisms also have 20 different cytoplasmic aaRSs, and generally also encode a separate set of mitochondrial aaRSs. Each aminoacyl-tRNA synthetase enzyme recognizes and reacts with a specific amino acid and one or more tRNAs that recognize the codons specific for that amino acid (cognate tRNAs). The specificity of the aaRS for the amino acid is determined by protein-amino acid interactions, and the specificity of the aaRS for the tRNA is determined by protein-RNA interactions, using different sites on the aaRS.

Although the isolation of a complete aminoacyl-tRNA synthetase gene from an organism of the genus Mycobacterium has not been reported previously, tRNA synthetases of *E. coli* have been studied. Based on conserved sequences and structural motifs, the 20 tRNA synthetases are divided into two classes of 10 enzymes each (see, e.g., Burbaum, J. J. and P. Schimmel, *J. Biol. Chem.*, 266(26):16965–16968 (1991)). Class I enzymes, have an N-terminal nucleotide binding fold comprised of alternating β-strands and α-helices and a C-terminal domain that is rich in α-helices and that contains residues needed for interactions with the parts of the tRNA distal to the amino acid attachment site (Shepard, A., et al., *Proc. Natl. Acad. Sci. U.S.A.* 89:9964–9968 (1992); Hou, Y. -M., et al., *Proc. Natl. Acad. Sci. U.S.A.* 88:976–980 (1991)). Five enzymes—cysteinyl-, isoleucyl-, leucyl-, methionyl-, and valyl-tRNA synthetases—are grouped together because they are more closely related in sequence and arrangement of their domains to each other than to the other five members of class I (Hou, Y. -M., et al., *Proc. Natl. Acad. Sci. U.S.A.* 88:976–980 (1991); Eriani, G., et al., *Nucleic Acids Res.* 19:265–269 (1991)). Furthermore, the C-terminal domains of isoleucyl-, leucyl-, methionyl-, cysteinyl- and valyl-tRNA synthetases appear to have a common origin, which is distinct from the C-terminal domain found in other class I enzymes (Shiba, K., et al., *Proc. Natl. Acad. Sci. USA* 89:1880–1884 (1992); Shepard, A., et al., *Proc. Natl. Acad. Sci. U.S.A.* 89:9964–9968 (1992)). In *E.coli*, these five enzymes of class I vary in size from 461 to 951 amino acids and are active as monomers. The size variation is in large part explained by the variability in the lengths of the two insertions designated connective polypeptide 1 (CP1), which is inserted between the second α-helix and third β-strand of the nucleotide binding fold, and CP2, which is placed between the third α-helix and fourth β-strand (Starzyk, R. M., et al., *Science* 237:1614–1618 (1987)). In all of these enzymes, CP1 is the larger of the two insertions and varies in *E.coli* from 61 in cysteinyl-tRNA synthetase to 300 amino acids in isoleucyl-tRNA synthetase (Hou, Y. -M., et al., *Proc. Natl. Acad. Sci. USA* 88:976–980 (1991)). While a portion of CP1 may be deleted from isoleucyl-tRNA synthetase without loss of function (Starzyk, R. M., et al., *Science* 237:1614–1618 (1987)), this insertion is known to facilitate acceptor helix interactions in the related glutaminyl-tRNA synthetase whose three dimensional structure in complex with tRNA$^{Gln}$ has been determined by x-ray crystallography (Rould, M. A., et al., *Science* 246:1135–1142 (1989)). The variable size of the CP1 insertion in class I enzymes possibly reflects the different origins of the motifs recruited into the catalytic domain for acceptor helix interactions (Schimmel, P., et al., *Protein Science* 1:1387–1391 (1992)).

Aminoacyl-tRNA synthetases are believed to be among the earliest proteins to have arisen in evolution. For this reason, and because the fidelity of these enzymes for their substrates must be high to accurately carry out the genetic code in protein biosynthesis, biologists have long studied the structures of these enzymes and their interactions with their substrates. Because the amino acid sequences of the tRNA synthetases have diverged over evolutionary time, significant differences exist between the structures of the enzymes from mammals (e.g., human, bovine) and mammalian pathogens. These differences can be exploited by finding inhibitors of aaRS activity which specifically target a tRNA synthetase of a pathogenic organism, and which may further have specific antimicrobial activity.

Examples of such inhibitors are already known. Pseudomonic acid and furanomycin have been found to inhibit bacterial isoleucyl-tRNA synthetases (Hughes, J. and Mellows, G., *Biochem J.*, 176:305–318 (1978)). Pseudomonic acid, an antibiotic which is in use as a human therapeutic agent, significantly inhibits binding of isoleucine to *E. coli* isoleucyl-tRNA synthetase and competitively inhibits aminoacylation by the enzyme, while it only weakly inhibits the aminoacylation of yeast tRNA$^{Ile}$ by rat liver IleRS (Hughes, J. and Mellows, G., *Biochem. J.* 191:209–219 (1980)).

Isolation of a Gene Encoding Met tRNA Synthetase from *M. tuberculosis*

Two combinations of degenerate primers, Kiyo-12 (SEQ ID NO.10 ) and Kiyo-15(SEQ ID NO.13), as well as Kiyo-13 (SEQ ID NO.11) and Kiyo-15 (SEQ ID NO.13), (Table 1) successfully amplified a gene sequence from *M. kansasii* (SEQ ID NO.3) that encodes an N-terminal conserved region of Met tRNA synthetase by PCR (polymerase chain reaction) methodologies (Example 1). The corresponding PCR fragment from *M. tuberculosis* was obtained using all four combinations of the reverse and forward degenerate primers described in Table 1. Single PCR fragments from *M. tuberculosis* and *M. kansasii* genomic DNA with sizes of 522 and 588 basepairs (including the primers), respectively, were isolated by gel electrophoresis and cloned. The gene fragments were sequenced revealing a high G-C content of 63–65%, which is typical of mycobacterial genomes. A Southern hybridization experiment (Example 2), in which the 599 bp fragment shown in SEQ ID NO:3) which comprises the amplified *M. kansasii* sequence, was observed to hybridize to digested *M. tuberculosis* DNA and bacillus Calmette-Gueérin (BCG) genomic DNA, but not to *E.coli* genomic DNA, provided further support for the mycobacterial origins of the PCR fragment, and demonstrated DNA sequence homology among mycobacterial species. Random protein data base searches revealed matches to portions of Met tRNA synthetases from *B. stearothermophilus, T. thermophilus, S. cerevisiae,* and *E.coli* with homologies over those regions ranging from 35 to 50%.

A PCR fragment from *M. kansasii* was used to screen a λgt11 *M. tuberculosis* library (Example 3). Approximately 100,000 plaques were analyzed by hybridization with a [$^{32}$P]-labeled *M. kansasii* DNA probe yielding seven positive plaques. The plaque with the strongest signal was purified and amplified. A 6 kb insert was recovered by an EcoRI digestion of the phagemid DNA and cloned into the phagemid pBSKS+ vector for sequencing. Internal sequencing primers were designed based on the *M. tuberculosis* PCR fragment. These primers, as well as universal primers to the vector, were used to sequence the gene in a sequential manner in both directions (Example 4). The Met tRNA synthetase gene was located at least 1 kb away from each end of the insert. Based on random protein data base searches, one end of the insert aligned with p-amino benzoate synthase and anthranilate synthase, while the other end showed no significant homology to any deposited sequences.

Characterization of *M. tuberculosis* Met tRNA Synthetase

The gene encoding *M. tuberculosis* Met tRNA synthetase and its flanking regions were sequenced. SEQ ID NO:1 shows 2,290 base pairs of the sequence determined. An open-reading frame of 1,566 basepairs (including the TGA stop codon) was identified having a GTC start codon (SEQ ID NO:1, position 1). Non-ATG (AUG in the mRNA) initiation codons have been observed in *M. tuberculosis* genes as well as in other organisms. However, where a codon other than AUG has been observed, invariably, the amino acid used for initiation has been determined to be methionine (Varshney, U. and U. L. RajBhandary, *Proc. Natl. Acad. Sci. USA*, 87:1586–1590 (1990)). Accordingly, SEQ ID NO:2 shows a methionine at the N-terminus of the encoded protein. For expression in E.coli, the GTC at position 1 was altered to ATG. There is also an ATG codon at position 7 of SEQ ID NO:1 which could be used for initiation of translation. The gene was found to be G-C rich (64%), which is typical in mycobacteria.

The open-reading frame encodes a protein of 521 amino acids (SEQ ID NO:2), beginning translation from position 1 of SEQ ID NO:1. Alternatively, if translation is initiated from the ATG at position 7, the encoded protein is 519 amino acids in length. The protein was found to align most closely with Met tRNA synthetases from T. thermophilus and B. stearothermophilus. The N-terminal domain was relatively well conserved. The HIGH signature sequence of the class I family was represented by a homologous HVGH for the M. tuberculosis which compares well to the HIGH or HLGH found for Met tRNA synthetases from other species. The second signature sequence, KMSKS, as well as the conserved anticodon binding region which contains a PW in the amino acid sequence, were also found in the M. tuberculosis enzyme. The only notable difference in the N-terminal domain was the lack of a zinc finger motif which has been characterized in other prokaryotic Met tRNA synthetases in the CP1 domain. The conserved cysteine residues which comprise the zinc finger appeared to be replaced by serines, which are more typically found in the yeast Met tRNA synthetase enzymes.

The C-terminal region which contains the oligomerization domain of the protein is extremely divergent among all of the Met tRNA synthetases. The T. thermophilus and B. stearothermophilus enzymes are the only Met tRNA synthetases which exhibit any significant homology in their dimerization regions. Although the M. tuberculosis Met tRNA synthetase is most closely related to these enzymes, it appears to lack the entire dimerization domain. Specifically, the polypeptide is only 521 amino acids, and thus, is truncated relative to the other bacterial Met tRNA synthetases, which range from 616 to 677 amino acids. Instead, the C-terminal length of the M. tuberculosis Met tRNA synthetase more closely resembles the cytoplasmic and mitochondrial enzymes from S. cerevisaie in this regard. It has been well documented that the oligomerization region is dispensable for aminoacylation activity. Proteolytic cleavage or genetically engineered proteins resulting in a truncated monomeric Met tRNA synthetase exhibit full aminoacylation activity. (For structure-function studies on Met tRNA synthetases, see Fayat, G., et al., Eur. J. Biochem. 44:335–342 (1974), Blanquet, S., et al., Eur. J. Biochem. 44:343–351 (1974) and Lawrence, F., et al., Eur. J. Biochem. 36:234–243 (1973).)

Expression and Aminoacylation Activity of M. tuberculosis Met tRNA Synthetase

M. tuberculosis Met tRNA synthetase was expressed as seen on SDS-polyacrylamide gels of protein extracts from three different strains carrying different expression vectors (Example 4). The pSLM101 plasmid was constructed using a Bluescript®II KS vector which expresses the Met tRNA synthetase as a β-galactosidase fusion protein under the control of the lac promoter. Under the conditions used, protein production appeared to be unaffected by the presence or absence of IPTG (isopropyl-β-D-thiogalactopyranoside) induction. The protein size was estimated to be about 60 kD by comparison to SDS-PAGE gel molecular weight markers.

M. tuberculosis Met tRNA synthetase was also expressed as a fusion protein with a histidine tail (His tail-Met tRNA synthetase) using the pSLM301 plasmid which was constructed from pET-15b. (For methods, see pET System Manual, 3rd edition from Novagen, Madison, Wis. For review, see Arnold, F. H., Bio/Technology 9:151–156 (1991)). The His tail-Met tRNA synthetase was expressed under the T7 promoter in one hour after induction with IPTG. The protein was estimated to be about 62 kD and was primarily sequestered in inclusion bodies. The histidine tail can be used to facilitate protein purification by affinity chromatography. Commercially available nickel column chromatography material coordinates to the tail, which is composed of six histidines. The protein can be eluted with an imidazole competitor producing homogeneous protein in a single purification step. In pSLM301, the histidine tail of the fusion protein is linked to the N-terminus of Met tRNA synthetase by a sequence of amino acids which can be specifically cleaved by a thrombin protease. Release of the histidine tail by thrombin cleavage yields the Met tRNA synthetase with eight amino acids residues fused to its N-terminus.

M. tuberculosis Met tRNA synthetase was also expressed as a fusion protein with glutathione S-transferase (GST-Met tRNA synthetase) (see procedures manual from Pharmacia P-L Biochemicals, Inc.: GST Gene Fusion System, regarding use of pGEX expression vectors and glutathione-S-transferase fusion proteins (1993); see also, Smith, EP 0,293,348, published Nov. 11, 1988), using pSLM201, which was constructed from PGEX-4T-2. The fusion protein was expressed during a one hour induction period with IPTG under the pTac promoter and estimated to be about 90 kDa based on SDS-PAGE gel electrophoresis. The protein was purified to homogeneity over a glutathione agarose column by affinity chromatography as described in Example 5.

The purified M. tuberculosis GST-Met tRNA synthetase was determined to cross-aminoacylate E.coli tRNA$^{fMet}$ (Example 5; FIG. 1). Under the conditions used, the activity of the M. tuberculosis fusion protein was approximately 10–20% of that exhibited by partially purified E.coli methionyl-tRNA synthetase. Thrombin cleavage of the GST fusion protein, which would release the full-length Met tRNA synthetase, may enhance aminoacylation activity.

The production of active recombinant M. tuberculosis Met tRNA synthetase allows in vitro drug screening based on enzyme assays. Furthermore, the GST-Met tRNA synthetase can be immobilized on a commercially available glutathione agarose column or other suitable GST affinity matrix, providing a method of screening large numbers of compounds (e.g., from combinatorial chemical libraries) to select compounds that bind specifically to M. tuberculosis Met tRNA synthetase, which may be further assessed for inhibitory and antimicrobial activity. The expression vectors, such as pSLM101, can be used to express the heterologous Met tRNA synthetase in a metG null strain of E.coli, such as MN9261/pRMS615 (see Kim, S., et al., Proc. Natl. Acad. Sci. USA 90:10046–10050 (1993)). Complementation of the metG defect in such a strain provides a tester strain which can be used for the efficient and rapid screening of large libraries of compounds for potential inhibitors, as described in more detail below. In addition, expression of M. tuberculosis Met tRNA synthetase (or a fusion protein comprising the protein) in the MN9261/pRMS615 strain permits purification of the M. tuberculosis protein without contamination from E.coli wild type Met tRNA synthetase.

Complementation of a Defect in a Yeast Mitochondrial Met tRNA Synthetase Gene by an M. tuberculosis Met tRNA Synthetase Gene Strains of S. cerevisiae having mutations (e.g., point mutations) in nuclear PET genes (petite or pet mutants), whose expression is required for the morphogenesis of respiratory-competent mitochondria, cannot grow on nonfermentable carbon sources such as glycerol media. However, because *S. cerevisiae* is a such facultative anaerobe, such strains are capable of growing on fermentable carbon sources such as glucose, in the absence of mitochondrial function. On rich media such as glucose, these "petite" strains exhibit the small colony phenotype for which they are named. The majority of mitochondrial proteins, including the mitochondrial aminoacyl-tRNA synthetases, are nuclear encoded, synthesized in the cytoplasm and imported into mitochondria. Petite mutants of *S. cerevisiae* having defects in genes encoding a mitochondrial aminoacyl-tRNA synthetases have been identified (see e.g., Tzagoloff, A. and A. M. Myers, *Ann. Rev. Biochem.* 55:249–285 (1986); Tzagoloff, A. and C. L. Diekmann, *Microbiol. Rev.* 54(9):211–225 (1990); Myers, A. M., et al., *EMBO J.* 4(8):2087–2092 (1985)).

Although pet strains having mutations in nuclear genes encoding components of the mitochondrial translational apparatus, such as mitochondrial aminoacyl-tRNA synthetase genes, can grow on glucose, these strains tend to lose their mitochondrial DNA at high frequency, converting to rho– or rho° strains, with large deletions in their mitochondrial DNA (rho–) or no mitochondrial DNA (rho°) (Tzagoloff, A. and A. M. Myers, *Ann. Rev. Biochem.* 55:249–285 (1986); Myers, A. M., et al., *EMBO J.* 4(8):2087–2092 (1985)). Therefore, for complementation studies with strain QBY42 (msm1-1), having a mutation in the nuclear gene encoding mitochondrial Met tRNA synthetase, the starting culture was first checked for the presence of intact mitochondria by crossing it with a test strain (QBY51) lacking mitochondrial DNA (rho°). Diploid progeny formed from such a cross were checked for growth on a nonfermentable substrate (YEPG; containing glycerol as carbon source). QBY42 haploid colonies bearing intact mitochondria (rho+) were identified by their ability to form a diploid able to grow on YEPG when crossed to QBY51, and rho+ haploids were used for transformation.

Strain QBY42 (rho+) was transformed with plasmids pQB104, pQB141 and pQB142, all expressing the wild type MSM1 gene, and plasmids pQB116 and pQB150 expressing the methionyl tRNA synthetase genes from *E.coli* and *M. tuberculosis*, respectively (Example 6). Cells bearing plasmids were obtained by selection on synthetic complete medium lacking uracil (SC minus Ura), and single colonies were tested for growth on YEPG plates. Functional complementation was scored as the ability of a given tRNA synthetase expressed from a plasmid to allow growth of the host strain on YEPG.

Two separate transformation experiments were carried out. In the first experiment, complementation was observed with genes derived from *E.coli* (carried by pQB116) and *M. tuberculosis* (carried by pQB150), but not with the positive control plasmids (pQB104, pQB141 or pQB142). Crossing with a rho° tester strain revealed that the pQB104, pQB141 and pQB142 transformants were all rho– and as such, unable to show complementation. In the second transformation experiment, care was taken to start with a culture that had a high proportion of rho+ cells; complementation with the control plasmids encoding MSM1 was observed as expected.

The above experiment was repeated, then, plasmid loss was induced on 5-FOA (5-fluoroorotic acid) plates, and cured strains were checked to show that the growth on YEPG was dependent on the presence of the plasmid. As an additional measure, the plasmid was extracted from yeast cells bearing the *M. tuberculosis* gene on plasmid pQB150 to verify its identity by restriction analysis.

Disruption strain QBY43 (aW303∇msm1) (MATa ade2-1 his3-11,15 leu2-3,112 ura3-1 trp1-1 msm1::HIS3; see Tzagoloff, A., et al., *Eur. J. Biochem.*, 179:365–371 (1989)), which contains an insertion within the MSM1 gene, was also used in these studies. QBY43 (aW303∇msm1) was crossed with strain QBY4 to form a diploid, which was used as a host cell for transformation. The diploid was transformed with the positive control plasmids (pQB104, pQB141 or pQB142), and plasmids pQB116, pQB150 and pQB151. The transformants were sporulated (on sporulation medium plus adenine, leucine and tryptophan), and the resulting tetrads were dissected. Ura+His+ spores (Ura+ indicating the presence of vector, His+ indicating the presence of the msm1::HIS3 allele) were recovered from diploids transformed with plasmids pQB116, pQB150 or pQB151, and were found to grow on YEPG medium, further confirming the complementation results observed in the msm-1 strain.

These studies demonstrate that methionyl-tRNA synthetase from both *E.coli* and *M. tuberculosis* can complement a defective yeast mitochondrial enzyme in vivo. The yeast strains having a defect in the endogenous mitochondrial Met-tRNA synthetase gene (msm1-1 or msm1::HIS3), further comprising a vector encoding an *M. tuberculosis* methionyl-tRNA synthetase (Met-tRNA synthetase having a mitochondrial targeting sequence fused to the N-terminus, or Met-tRNA synthetase having a mitochondrial targeting sequence and GST portion fused to the N-terminus) capable of complementing the endogenous defect, are examples of yeast mitochondrial tester strains which can be used to test the effects of inhibitors on *M. tuberculosis* methionyl-tRNA synthetase.

Nucleic Acids, Constructs and Vectors

The present invention relates to isolated and/or recombinant (including, e.g., essentially pure) nucleic acids having sequences which encode a mycobacterial methionyl-tRNA synthetase, or a portion of a mycobacterial methionyl-tRNA synthetase. In one embodiment, the nucleic acid or portion thereof encodes a protein or polypeptide having at least one function characteristic of a mycobacterial methionyl-tRNA synthetase, such as a catalytic activity (e.g., catalysis of aminoacyl-adenylate formation, catalysis of aminoacylation of a tRNA with methionine) and/or binding function (e.g., tRNA-, amino acid-, or ATP-binding). The present invention also relates more specifically to isolated and/or recombinant nucleic acids or a portion thereof having sequences which encode methionyl-tRNA synthetase of *M. tuberculosis* or a portion thereof.

The invention further relates to isolated and/or recombinant nucleic acids that are characterized by (1) their ability to hybridize to a nucleic acid having the sequence SEQ ID NO:1 (having a GTC codon at positions 1–3 as shown, or an ATG codon at positions 1–3) or its complement, or to a portion thereof comprising nucleotides 1–1566 or its complement, or (2) by their ability to encode a polypeptide of the amino acid sequence SEQ ID NO:2 or functional equivalents thereof (i.e., a polypeptide which aminoacylates the isoaccepting cognate methionine tRNAs of *M. tuberculosis* with methionine), or (3) by both characteristics. In one embodiment, the percent amino acid sequence similarity between SEQ ID NO:2 and functional equivalents thereof is at least about 40% (≧40%). In a preferred embodiment, functional equivalents of SEQ ID NO:2 share at least about 50% sequence similarity with SEQ ID NO:2. More preferably, the percent amino acid sequence similarity between SEQ ID NO:2 and functional equivalents thereof is at least about 60%, and still more preferably, at least about 70%. Isolated and/or recombinant nucleic acids meeting these criteria comprise nucleic acids having sequences identical to sequences of naturally occurring mycobacterial MetRS and portions thereof, or variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues.

Such nucleic acids can be detected and isolated under high stringency conditions or moderate stringency conditions, for example. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, depending in part upon the characteristics of the known DNA to which other unknown nucleic acids are being compared for homology.

Isolated and/or recombinant nucleic acids that are characterized by their ability to hybridize to a nucleic acid having the sequence SEQ ID NO: 1 or its complement (e.g. under high or moderate stringency conditions) may further encode a protein or polypeptide having at least one function characteristic of a mycobacterial methionyl-tRNA synthetase, such as a catalytic activity (e.g., aminoacyladenylate formation, aminoacylation of a tRNA with methionine) and/or binding function (e.g., tRNA-, amino acid-, or ATP-binding). The catalytic or binding function of a protein or polypeptide encoded by hybridizing nucleic acid may be detected by standard enzymatic assays for activity or binding (e.g., assays which monitor aminoacyladenylate formation, aminoacylation of tRNA). Functions characteristic of methionyl-tRNA synthetase may also be assessed by in vivo complementation activity, or other suitable methods. Enzymatic assays, complementation tests, or other suitable methods can also be used in procedures for the identification and/or isolation of nucleic acids which encode a polypeptide of the amino acid sequence SEQ ID NO: 2 or functional equivalents thereof.

Nucleic acids of the present invention can be used in the production of proteins or polypeptides. For example, DNA containing all or part of the coding sequence for mycobacterial methionyl-tRNA synthetase, or DNA which hybridizes to the sequence SEQ ID NO: 1, and having either an ATG or GTC initiation codon, or its complement, can be incorporated into various constructs and vectors created for further manipulation of sequences or for production of the encoded polypeptide in suitable host cells.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501. The aminoacyl-tRNA synthetases are known to have different quaternary structures, including both monomeric and multimeric structures (e.g., homodimers, tetramers and heteromultimeric $\alpha_2\beta_2$ forms). Thus, as used herein, a nucleic acid which encodes a portion of a mycobacterial methionyl- or aminoacyl-tRNA synthetase can also refer to one of two or more distinct subunits of said tRNA synthetase.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In one embodiment, the antisense nucleic acid is wholly or partially complementary to and can hybridize with a target nucleic acid, wherein the target nucleic acid can hybridize to a nucleic acid having the sequence of the complement of SEQ ID NO:1. For example, antisense nucleic acid can be complementary to a target nucleic acid having the sequence of SEQ ID NO: 1 or a portion thereof sufficient to allow hybridization. In another embodiment, the antisense nucleic acid is wholly or partially complementary to and can hybridize with a target nucleic acid which encodes a mycobacterial methionyl-tRNA synthetase (e.g., *Mycobacterium tuberculosis* MetRS).

*M. tuberculosis* is the major causative agent of infectious tuberculosis in humans. Because advances in the understanding and treatment of this disease would be of tremendous benefit, it was the mycobacterial species selected for most of the experimental work described herein. However, the approaches described to isolate and manipulate the MetRS gene of *M. tuberculosis*, to construct vectors and host strains, and to produce and use the MetRS enzyme, can be applied to other members of the genus of Mycobacteria, including, but not limited to, pathogenic strains such as *M. leprae, M. kansasii, M. avium, M. intracellulare, M. bovis,* and *M. paratuberculosis,* or fast-growing, non-pathogenic strains such as *M. smegmatis.* The entire *M. tuberculosis* methionyl-tRNA synthetase gene described here, or sufficient portions thereof, including the fragments within the coding sequence which were produced by PCR, or the *M. kansasii* PCR fragment described herein, can be used as a probe in hybridization experiments to detect and recover homologous genes of the other mycobacterial species. This can be achieved using the procedures described herein or other suitable methods.

Proteins

The invention also relates to proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in mycobacterial cells. "Isolated" proteins or polypeptides include proteins or polypeptides obtained by methods described herein, similar methods or other suitable methods, including essentially pure proteins or polypeptides, proteins or polypeptides produced by chemical synthesis, or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein has at least one function characteristic of a mycobacterial methionyl-tRNA synthetase, such as a catalytic activity (e.g., catalysis of aminoacyl-adenylate formation, catalysis of aminoacylation of a tRNA with methionine) and/or binding function (e.g., tRNA-, amino acid-, or ATP-binding). As such, these proteins are referred to as methionyl-tRNA synthetases of mycobacterial origin or mycobacterial methionyl-tRNA synthetases, and include, for example, naturally occurring mycobacterial methionyl-tRNA synthetases, variants of those proteins and/or portions thereof. Such variants include mutants differing by the addition, deletion or substitution of one or more amino acid residues, or modified polypeptides in which one or more residues is modified, and mutants comprising one or more modified residues.

In a particularly preferred embodiment, like naturally occurring mycobacterial methionyl-tRNA synthetases, the mycobacterial methionyl-tRNA synthetases of the present invention aminoacylate the isoaccepting cognate methionine tRNAs of the mycobacterium with methionine in a two-step reaction. For example, in the case of *M. tuberculosis*, an isolated mycobacterial methionyl-tRNA synthetase is able to aminoacylate each of the isoaccepting species of cognate tRNA$^{Met}$ of *M. tuberculosis* with methionine. In the first step, mycobacterial methionyl-tRNA synthetase catalyzes the covalent linkage of methionine to ATP to form an adenylate complex (methionyl-adenylate) with the release of pyrophosphate, and, in a second step, catalyzes the covalent linkage of methionine to a specific tRNA recognized by the enzyme, releasing AMP.

The invention further relates to fusion proteins, comprising a mycobacterial methionyl-tRNA synthetase (as described above) as a first moiety, linked to second moiety not occurring in the mycobacterial MetRS as found in nature. Thus, the second moiety can be an amino acid or polypeptide. The first moiety can be in an N-terminal location, C-terminal location or internal to the fusion protein. In one embodiment, the fusion protein comprises an *M. tuberculosis* methionyl-tRNA synthetase as the first moiety, and a second moiety comprising a linker sequence and affinity ligand.

Fusion proteins can be produced by a variety of methods. For example, some embodiments can be produced by the insertion of a MetRS gene or portion thereof into a suitable expression vector, such as Bluescript®II SK ± (Stratagene), pGEX-4T-2 (Pharmacia) and pET-15b (Novagen). The resulting construct is then introduced into a suitable host cell for expression. Upon expression, fusion protein can be purified from a cell lysate by means of a suitable affinity matrix (see e.g., Examples 4 and 5; *Current Protocols in Molecular Biology* (Ausubel, F. M. et al., eds., Vol. 2, Suppl. 26, pp. 16.4.1–16.7.8 (1991)).

The invention also relates to isolated and/or recombinant portions of a methionyl-tRNA synthetase of mycobacterial origin. A portion of a mycobacterial methionyl-tRNA synthetase can also refer to one of two or more distinct subunits of said tRNA synthetase. Portions of the enzyme can be made which have full or partial function on their own, or which when mixed together (though fully, partially, or nonfunctional alone), spontaneously assemble with one or more other polypeptides to reconstitute a functional protein having at least one function characteristic of a mycobacterial methionyl-tRNA synthetase. (See, e.g., Shiba, K. and Schimmel, P., *J. Biol. Chem.* 267:22703–22706 (1992) for an example of three inactive peptides from *E. coli* IleRS spontaneously assembling in vivo to reconstitute active enzyme; see also, Burbaum, J. and Schimmel, P., *Biochemistry* 30(2):319–324 (1991), describing non-overlapping segments of *E.coli* MetRS which can fold together to reconstitute an active enzyme capable of recognizing and charging tRNA in vitro and in vivo). Portions of the enzyme having at least one function characteristic of methionyl-tRNA synthetase, such as a catalytic and/or binding function, can be made. Extensive studies on the structure and function of the aaRSs provide the basis for being able to divide the mycobacterial MetRS enzymes into functional domains (Schimmel, P., *Current Biology* 1:811–816 (1991)).

The sequences and structures of the catalytic domain of tRNA synthetases already purified and studied are the basis for dividing them into two distinct classes of ten enzymes each, Class I and Class II (Schimmel, P., *Ann. Rev. Biochem.* 56:125–158 (1987); Webster, T. A., et al., *Science* 226:1315–1317 (1984); Eriani, G. et al., *Nature* 347:203–206 (1990) and Cusack, S., et al., *Nature* 347:249–255 (1990)). Class I enzymes have a well-conserved N-terminal nucleotide binding fold responsible for amino acid binding, aminoacyladenylate formation, and tRNA acceptor helix docking. Within this domain are CP1 and CP2, segments of non-conserved amino acid sequence of lengths varying with the species of origin. Studies of the function of mutant aaRS gene products and analyses of the aligned amino acid sequences of aaRSs have revealed conserved and nonconserved regions and likely sites for interactions with other molecules (Shepard, A., et al., *Proc. Natl. Acad. Sci. USA* 89:9964–9968 (1992)). Extensive deletions could be made in the CP1-encoding region of the IleRS gene of *E. coli* without destroying activity of the mutant enzyme (Starzyk, R. M., et al., *Science* 237:1614–1618 (1987)), for example.

Joined to the class-defining domain is a second domain, idiosyncratic to the tRNA synthetase, which provides interactions with the parts of the tRNA which are distal to the amino acid attachment site. In some tRNA synthetases, this second domain interacts directly with the anticodon (Rould, M. A. et al., *Science* 246:1135–1142 (1989) and Cavarelli, J., et al., *Nature* 362:181–184 (1993)), while in other enzymes there is no contact made between the second domain and the anticodon (Biou, V., et al., *Science* 263:1404–1410 (1994)). To a first approximation, the two domains in Class I,tRNA synthetases interact with the two distinct domains of the L-shaped tRNA structure. Thus, the recognition elements of the tRNA synthetase and of the tRNA which are needed for the operational RNA code are segregated into discrete protein and RNA domains.

Method of Producing Recombinant Mycobacterial MetRSs

Another aspect of the invention relates to a method to produce mycobacterial methionyl-tRNA synthetase or a portion thereof and an expression system and host cells containing a vector appropriate for expression of the mycobacterial methionyl-tRNA synthetase.

Cells that express a recombinant mycobacterial methionyl-tRNA synthetase or a portion thereof can be made and grown in culture to produce the enzyme for isolation and purification. These cells can be procaryotic or eucaryotic.

Examples of procaryotic cells that can be used to express mycobacterial methionyl-tRNA synthetases include *Escherichia coli, Bacillus subtilis* and other bacteria. Examples of eucaryotic cells that can be used to express mycobacterial methionyl-tRNA synthetases include yeasts, such as *Saccharomyces cerevisiae*, and other lower eucaryotic cells, and cells of higher eucaryotes such as those from insects and mammals. (See, e.g., Ausubel, F. M. et al., eds. *Current Protocols in Molecular Biology*, Greene Publishing Associates and John Wiley & Sons Inc., (1993)).

To make host cells that produce a recombinant mycobacterial MetRS protein or portion thereof for isolation and purification, as a first step the gene encoding the MetRS can be inserted into a nucleic acid vector, e.g., a DNA vector, such as a plasmid, virus or other suitable replicon, which can be present in a single copy or multiple copies, or the gene can be integrated in a host cell chromosome. Such a suitable replicon contains all or part of the coding sequence for mycobacterial methionyl-tRNA synthetase, and has the coding sequence under the control of transcription signals and linked to appropriate translation signals to permit translation of the MetRS, portion thereof, or of a fusion protein comprising MetRS or portion thereof. As a second step, the vector can then be introduced into cells by a method appropriate to the type of host cells (e.g., transformation, electroporation, infection). In a third step, for expression from the methionyl-tRNA synthetase gene, the host cells can be maintained under appropriate conditions, e.g., in the presence of inducer, normal growth conditions, etc.).

As a particular example of the above approach to ultimately producing active mycobacterial methionyl-tRNA synthetase, a gene encoding the mycobacterial MetRS can be integrated into the genome of a virus that enters the host cells. By infection of the host cells, the components of a system which permits the transcription and translation of the mycobacterial aaRS gene are present in the host cells. Alternatively, an RNA polymerase gene, inducer, or other component required to complete such a gene expression system may be introduced into the host cells already containing the mycobacterial MetRS gene, for example, by means of a virus that enters the host cells and contains the required component. The mycobacterial MetRS gene can be under the control of an inducible or constitutive promoter. The promoter can be one that is recognized by the non-mycobacterial host cell RNA polymerase. The promoter can, alternatively, be one that is recognized by a viral RNA polymerase and is transcribed following infection of the host cells with a virus.

Antibodies

The invention further relates to antibodies raised against an isolated and/or recombinant mycobacterial methionyl-tRNA synthetase, including portions thereof (e.g., a peptide), which can specifically recognize and bind to the enzyme. These can be used in methods to purify the protein or portions thereof, or to selectively inactivate one of the enzyme's active sites, or to study other aspects of the enzyme's structure, for example. The term antibody is intended to encompass both polyclonal and monoclonal antibodies. The term antibody is also intended to encompass whole antibodies, biologically functional fragments thereof, and chimeric and humanized antibodies comprising portions from more than one species. Biologically functional antibody fragments which can be used are those fragments sufficient for binding of the antibody fragment to a mycobacterial MetRS to occur, such as Fab, Fv, Fab' and F(ab')$_2$ fragments. The chimeric antibodies can comprise proteins derived from two different species. The portions derived from two different species can be joined together chemically by conventional techniques or can be prepared as a single contiguous protein using genetic engineering techniques (See, e.g., Cabilly et al., U.S. Pat. No. 4,816,567, Neuberger, M. S. et al., WO 86/01533 and Winter, G. P., EP 0,239,400). DNA encoding the proteins of both portions of the chimeric antibody can be expressed to produce a contiguous protein.

Assays for Inhibitors and Tester Strains

The enzymatic assays, binding assays, and construction of tester strains described below, which rely upon the nucleic acids and proteins of the present invention, can be used, alone or in combination with each other or other suitable methods, to identify inhibitors of one or more mycobacterial methionyl-tRNA synthetases.

Enzyme Assay

Upon the isolation of an aaRS gene from mycobacteria, the gene can then be put into an expression system for production, followed by isolation and testing of the enzyme in vitro. The isolated or purified mycobacterial aaRS can also be used in further structural studies that will allow for the design of antibiotics which specifically target the aaRS of mycobacteria, while not affecting or minimally affecting the mammalian (e.g., human) aaRSs. The design of these drugs will exploit the structural differences between the pathogen aaRS and the aaRSs of mammals, such as humans.

Furthermore, isolated, active mycobacterial aaRSs can be used in an in vitro method of screening for inhibitors of aminoacyl-tRNA synthetase activity in which the inhibitory effect of a compound is assessed by monitoring MetRS activity according to standard techniques. For example, inhibitors of isolated, active mycobacterial MetRS can be identified by the method. In one embodiment, the isolated enzyme is maintained under conditions suitable for methionyl-adenylate formation, the enzyme is contacted with a compound to be tested, and formation of the aminoacyladenylate is monitored by standard assay. A reduction in the activity measured in the presence of compound, as compared with the activity in the absence of compound, is indicative of inhibition of MetRS activity by the compound. In another embodiment, formation of methionyl-tRNA$^{Met}$ is monitored in a standard aminoacylation assay. Inhibitors identified by enzymatic assay can be further assessed for antimicrobial activity using tester strains as described herein, or other suitable assays.

Binding Assay

Isolated, recombinant aaRS or a portion thereof, and suitable fusion proteins can be used in a method to select and identify compounds which bind specifically to mycobacterial aaRSs, such as *M. tuberculosis* Met tRNA synthetase, and which are potential inhibitors of aaRS activity. Compounds selected by the method can be further assessed for their inhibitory effect on aaRS activity and for antimicrobial activity.

In one embodiment, isolated or purified mycobacterial MetRS can be immobilized on a suitable affinity matrix by standard techniques, such as chemical cross-linking, or via an antibody raised against the isolated or purified mycobacterial MetRS and bound to a solid support. The matrix is packed in a column or other suitable container and is contacted with one or more compounds (e.g., a mixture) to be tested under conditions suitable for binding of compound to the MetRS. For example, a solution containing compounds is made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more substrates or substrate analogs which can disrupt binding of compound to the aaRS, such as methionine, ATP, tRNA$^{Met}$ for MetRS, or other suitable molecules which competitively inhibit binding).

Fusion proteins comprising all of, or a portion of, a mycobacterial aaRS linked to a second moiety not occurring in the mycobacterial aaRS as found in nature (see above), can be prepared for use in another embodiment of the method. Suitable fusion proteins for this purpose include those in which the second moiety comprises an affinity ligand (e.g., an enzyme, antigen, epitope). The fusion proteins can be produced by the insertion of a mycobacterial aaRS gene or portion thereof into a suitable expression vector, which encodes an affinity ligand (e.g., pGEX-4T-2 and pET-15b, encoding glutathione-S-transferase and His-Tag affinity ligands, respectively). The expression vector is introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

In one aspect of this embodiment, the fusion protein is immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the aaRS portion of the bound fusion protein. Next, the affinity matrix with bound fusion protein is washed with a suitable wash buffer to remove unbound compounds and non-specifically bound compounds. Compounds which remain bound can be released by contacting the affinity matrix with fusion protein bound thereto with a suitable elution buffer (a compound elution buffer). Wash buffer is formulated to permit binding of the fusion protein to the affinity matrix, without significantly disrupting binding of specifically bound compounds. In this aspect, compound elution buffer is formulated to permit retention of the fusion protein by the affinity matrix, but is formulated to interfere with binding of the compound (s) tested to the aaRS portion of the fusion protein. For example, a change in the ionic strength or pH of the elution buffer can lead to release of compounds, or the elution buffer can comprise a release component or components designed to disrupt binding of compounds to the aaRS portion of the fusion protein (e.g., one or more substrates or substrate analogs which can disrupt binding of compounds to the aaRS portion of the fusion protein, such as methionine, ATP, tRNA$^{Met}$ for MetRS, or other suitable molecules which competitively inhibit binding).

Immobilization can be performed prior to, simultaneous with or after contacting the fusion protein with compound as appropriate. Various permutations of the method are possible, depending upon factors such as the compounds tested, the affinity matrix-ligand pair selected, and elution buffer formulation. For example, after the wash step, fusion protein with compound bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

To enrich for specific binding to the aaRS portion of the fusion protein, compounds can be pre-treated, for example with affinity matrix alone, with affinity ligand or a portion thereof (e.g., the portion present in the fusion protein), either alone or bound to matrix, under conditions suitable for binding of compound to the aaRS portion of the bound fusion protein.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also Rebek et al., Process for Creating Molecular Diversity, U.S. Ser. No. 08/180,215, filed Jan. 12, 1994, relating to compounds without tags; see also, Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

Random sequence RNA and DNA libraries (see Ellington, A. D. et al., *Nature* 346: 818–822 (1990); Bock, L. C. et al., *Nature* 355: 584–566 (1992); and Szostak, J. W., *Trends in Biochem. Sci.* 17:89–93 (March, 1992)) can also be screened according to the present method to select RNA or DNA molecules which bind to an aaRS, such as *M. tuberculosis* MetRS. Such molecules can be further assessed for antimicrobial effect upon introduction into a cell (e.g., by expression in the case of an RNA molecule selected by the method).

Tester Strains

Nucleic acids of the present invention can also be used in constructing tester strains for in vivo assays of the effect on the activity of the mycobacterial enzyme of a substance which is added to tester strain cells. A tester strain comprises a host cell having a defect in a gene encoding a mycobacterial aaRS, and a heterologous mycobacterial aaRS gene which complements the defect in the host cell gene. Thus, complementation of a particular defective host cell aaRS gene by a heterologous mycobacterial aaRS gene is a threshold requirement for a tester strain. Because the aaRS genes are essential, the heterologous gene can be introduced into the host cell simultaneously with inactivation of the host cell gene to preserve viability. Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

For example, temperature sensitive alleles of the genes encoding cytoplasmic IleRS and MetRS have been described in *S. cerevisiae* (Hartwell, L. H., and McLaughlin, C. S., *J. Bacteriol.* 96:1664–1671 (1968)), and are available from the Yeast Genetic Stock Center (University of California-Berkeley; catalog nos. 342 and 19:3:4, respectively). Temperature sensitive serS strains of *E. coli* have also been described (Low, B., et al., *J. Bacteriol.* 108:742-750 (1971); Clarke, S. J. et al., *J. Bacteriol.* 113:1096-1103 (1973)).

If the heterologous gene complements the inactivated host cell gene, such a cell can be used in a test of whether a substance that enters the cells specifically interacts with the mycobacterial tRNA synthetase (or a component in the pathway of tRNA synthetase gene expression) introduced for testing, to cause loss of function of the tested mycobacterial tRNA synthetase in those host cells. Thus, such cells are "tester strains." Successful cross-species complementation has been described already, for example, for yeast seryl-tRNA synthetase and for yeast isoleucyl-tRNA synthetase in *E. coli* (Weygand-Durasevic, I., et al., *Eur. J. Biochem* 214:869-877 (1993); Racher, K. I., et al., *J. Biol. Chem.* 266:17158-17164 (1991)). Cross-species complementation within the genus Mycobacterium can also serve as the basis for testing, for example, the aaRS enzymes of *M. tuberculosis* in *M. smegmatis*.

In tester cells to be used in an assay for chemical substances that can inhibit the function of a specific mycobacterial aaRS, the gene for the mycobacterial tRNA synthetase can, for example, physically replace the host cell aaRS gene or can be present in addition to a host aaRS gene that does not produce a functional product, and the mycobacterial gene whose gene product is to be tested complements the host gene. A substance to be tested is administered to the tester cells, and the viability or growth of such cells can be compared with that of cells of a suitable control.

Suitable host cells can be mycobacterial or non-mycobacterial host cells. As a tester strain comprises a host cell comprising a heterologous mycobacterial aaRS gene (i.e., one from a heterologous species), a suitable mycobacterial host cell is heterologous with respect to the species from which the mycobacterial gene to be tested is isolated. One feature of using a heterologous mycobacterial species as a host cell in a tester strain is that mycobacterial species are likely be more similar to each other than to non-mycobacterial species with respect to their enzymatic and structural composition. *M. smegmatis* or other fast growing, non-pathogenic species of mycobacteria, are preferred mycobacterial species to use as hosts for the construction of tester strains such as those comprising a *M. tuberculosis* MetRS gene.

Preferred non-mycobacterial species to use as hosts for the construction of tester strains are *E. coli, S. cerevisiae,* and *B. subtilis*. These species are especially amenable to genetic manipulation because of their history of extensive study.

Suitable host cells having a genotype useful for the construction of a tester strain can be constructed or selected using known methods. For example, both in *E. coli* and in *S. cerevisiae*, a first plasmid which contains a functional copy of a host chromosomal aaRS gene which is to be inactivated later, along with some selectable marker gene, can be constructed and introduced into cells. Then, an inactivating mutation can be caused in the chromosomal copy of the aaRS gene. One way to do this is by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin et al., U.S. Pat. No. 4,713,337; Schimmel, P., U.S. Pat. No. 4,963,487; Toth, M. J. and Schimmel., P., *J. Biol. Chem.* 261(15):6643-6646 (1986); Rothstein, R., *Methods in Enzymology* 194:281-301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS. A test plasmid which is compatible with the maintenance plasmid, and which contains a mycobacterial aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluoroorotic acid to select against *S. cerevisiae* cells which have a first plasmid containing the URA3 gene), cells which survive by virtue of having a complementing mycobacterial aaRS gene on the second plasmid can be selected (Sikorsky, R. S. and Boeke, J. D., *Methods in Enzymology* 194:302-318 (1991)).

A number of *E. coli* strains already exist in which an aaRS gene has been inactivated by some method, in whole or in part, yielding an observable phenotypic defect which can be detectably complemented. For example, a null strain in which the gene encoding MetRS has been inactivated, and a mutant strain of *E. coli* in which the gene encoding MetRS has been conditionally inactivated, have been described (see Kim, et al., *Proc. Natl. Acad. Sci. USA* 90:10046-10050 (1993), describing a metG null strain of *E. coli* carrying a maintenance plasmid, MN9261/pRMS615); and Barker, D. G. et al. *Eur. J. Biochem.* 127:449-457 (1982) and Starzyk, R. M. et al., *Biochemistry*, 28:8479-8484 (1989), regarding a mutant strain having a methionine auxotrophy because the $K_m$ for methionine of the enzyme encoded by the chromosomal MetG allele is elevated).

Several *S. cerevisiae* strains have been constructed in which a gene encoding a mitochondrial aaRS has been inactivated (see, e.g., Edwards et al., *Cell* 51:643-649 (1987)), or a cytoplasmic aaRS has been cloned on a vector (see, e.g., Ludmerer et al., *J. Biol. Chem.* 262:10801-10806 (1987)). Mitochondrial mutant strains such as the msm1-1 strain and disruption strain QBY43 (aW303ΔMSM1) (MATa ade2-1 his 3-11, 15 leu2-3,112 ura3-1 trp1-1 msm1::HIS3; see Tzagoloff, A., et al., *Eur. J. Biochem,* 179:365-371 (1989)) described above can be used for the construction of yeast tester strains for testing a mycobacterial MetRS (see also Example 6).

The pathogenicity and long generation time of Mycobacterium tuberculosis (24 h) are major obstacles in the genetic manipulation of this organism. Thus, in another embodiment, a fast growing species of mycobacteria, such as *Mycobacterium smegmatis* (2-3 h), can be used as a host to construct a tester strain.

For example, an *M. smegmatis* host cell having a defect in the endogenous MetRS can be constructed. The methionyl-tRNA synthetase gene from *M. smegmatis* can be obtained and analyzed (e.g., by restriction mapping, sequence analysis) in order to identify a suitable site or sites for the insertion of a spectinomycin resistance cassette or other suitable marker gene to disrupt expression of the gene. The cassette can inserted into the *M. smegamatis* MetRS gene to disrupt the gene at a single site (e.g., by ligation into a particular restriction site) or can replace all or part of the gene (e.g., by ligation into two restriction sites, with deletion of intervening *M. smegmatis* MetRS gene sequences). The resulting construct can be introduced into the *M. smegmatis* host by suitable methods, and homologous recombination between flanking sequences in the construct and on the chromosome leads to inactivation of the *M. smegmatis* gene. Introduction of a heterologous mycobacterial aaRS gene which can complement the host cell defect prior to or simultaneous with inactivation can yield a tester strain.

For example, a linear fragment comprising the *M. smegmatis* gene disrupted by the insertion of a spectinomycin resistance cassette can be used to electroporate *M. smegmatis*. Homologous recombination between this construct and the wild type gene on the chromosome can occur (Husson, R. N., et al., *J. Bacteriol.* 172:519–524 (1990)), inactivating the host gene. Simultaneous with the introduction of the linear fragment, *M. smegmatis* can be transformed with a suitable rescue plasmid, such as pAL5000 (Labidi, A., et al., *Curr. Microbiol.* 11:235–240 (1984)) into which a heterologous mycobacterial (e.g., *M. tuberculosis*) methionyl-tRNA synthetase gene has been cloned, which replicates in mycobacteria. Selection of transformants can be performed on 7H media (formulated for the growth of *M. smegmatis*; see Husson, R. N., et al., *J. Bacteriol.* 172:519–524 (1990)) containing spectinomycin.

In another approach, a linear fragment containing the *M. smegmatis* gene disrupted by the insertion of a spectinomycin resistance cassette can be cloned into a pUC vector or other suitable vector which does not replicate in mycobacteria (see, e.g., Yanisch-Perron, C., et al., *Gene* 33:103–119 (1985) regarding pUC vectors). The resulting nonreplicable vector can be used to electroporate *M. smegmatis* simultaneously with a suitable rescue plasmid, such as pAL5000 into which a heterologous mycobacterial (e.g., *M. tuberculosis*) methionyl-tRNA synthetase gene has been cloned. The nonreplicable vector will be lost; however, cells in which recombination between the wild type gene on the chromosome and the disrupted gene present on the nonreplicable vector has occurred prior to loss of the construct, leading to inactivation of the host cell MetRS gene, can be selected as indicated above.

Causing or selecting for a double crossover event which creates a deletion and insertion can be used in itself as a one-step method of constructing a tester strain in which a native aaRS gene is replaced by the corresponding mycobacterial gene whose gene product is to be tested. Endogenous recombination mechanisms have been used to advantage previously in *E. coli*, *B. subtilis*, *M. smegmatis*, and *S. cerevisiae*, among other organisms. This method depends on the ability of the mycobacterial gene to be tested to complement the native corresponding aaRS gene. This can be done by introducing into the cells double-stranded DNA having regions of homology to the DNA flanking the target native aaRS gene, and having between these regions a gene encoding a selectable marker as well as the mycobacterial aaRS gene intended to replace the native aaRS gene. The survival of cells expressing the selectable marker is indicative of expression of the introduced mycobacterial aaRS gene and complementation of the defect in the endogenous synthetase.

For example, a tester strain, useful for testing the effect of a compound on the function of MetRS expressed by an inserted *M. tuberculosis* gene, can be constructed in a one-step method. Optional positive and negative controls for this cross-species transformation can be used to show that the resulting strain depends on the MetRS gene from *M. tuberculosis* for growth and that this recombination event is not lethal. For example, *B. subtilis* cells made competent for transformation (Dubnau, D. and Davidoff-Abelson, R., *J. Mol. Biol.* 56:209–221 (1971)) can be transformed with a suitable construct, such as a linearized plasmid containing an insert. Generally, the construct includes a selectable marker gene for antibiotic resistance, or other suitable selectable marker. In one embodiment, a linearized plasmid which contains the *M. tuberculosis* MetRS gene and an antibiotic resistance gene, situated between sequences homologous to the flanking sequences of the endogenous MetRS gene of the host cells, is used to transform the host cell. For a positive control, the linearized plasmid can be constructed in a similar fashion, except that the native *B. subtilis* MetRS gene replaces the *M. tuberculosis* gene, such that a normal *B. subtilis* MetRS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous MetRS gene. Successful construction of a tester strain can also be confirmed by Southern analysis.

The yeast *S. cerevisiae* offers additional possibilities for genetic manipulations to create tester strains, relative to bacteria. For example, one-step gene disruptions can be performed in diploid cells using a DNA fragment comprising a copy of an aaRS containing a deletion of the aaRS gene and an insertion of a selectable marker in the deleted gene. For example, MES1, the gene encoding cytoplasmic methionyl tRNA synthetase from *S. cerevisiae*, has been cloned and sequenced (Fasiolo, F. et al., *J. Biol. Chem.* 260:15571–15576 (1985); Walter, P. et al., *Proc. Natl. Acad. Sci. USA* 80:2437–2441 (1983)). A suitable fragment can be introduced into a diploid cell to disrupt one chromosomal copy of the yeast gene. Successful integration of the deleted aaRS gene can be confirmed by Southern blotting and by tetrad analysis of the sporulated diploid cells. The diploid cells heterozygous for the chromosomal aaRS gene provide a diploid tester strain which can be transformed with a plasmid containing the mycobacterial aaRS gene. These cells can be sporulated and the haploid spores analyzed for rescue of the defective chromosomal aaRS by the mycobacterial aaRS gene.

In addition, those diploid cells that are found to contain one copy of the deleted chromosomal aaRS gene, as well as one functional copy, can be transformed with a maintenance plasmid which contains the corresponding wild type yeast aaRS gene and which provides for a mechanism to select against survival of the cells containing this plasmid. These cells can then be made to sporulate to obtain a haploid null strain containing the disrupted chromosomal aaRS gene and the wild type gene on the maintenance plasmid. This haploid tester strain can then be transformed with a test plasmid which expresses a mycobacterial aaRS gene, and the maintenance plasmid can be selected against by growing this strain under appropriate conditions.

Examples of convenient yeast vectors for cloning include those in the pRS400 series (Christianson, T. W., et al. *Gene* 110:119–122 (1992)), pDAD1 and pDAD2, which contain a GAL1 promoter (Davis, L. I. and Fink, G. R., *Cell* 61:965–978 (1990)) and pEG (Mitchell, D. A., et al. *Yeast* 9:715–723 (1993)).

In another embodiment, a eucaryotic host cell is used to construct a mitochondrial tester strain. For example, in yeast, each of the mitochondrial tRNA synthetases is essential for growth on non-fermentable carbon sources (e.g., glycerol). Thus, complementation tests can be conducted in mitochondrial tester strains. As the genes encoding mitochondrial aminoacyl-tRNA synthetases are typically nuclear-encoded, the procedures described above can be modified to construct mitochondrial tester strains, having a defect in a mitochondrial aminoacyl-tRNA synthetase. Modification is necessitated by the fact that yeast strains with a defect in mitochondrial protein synthesis, such as a defective aminoacyl-tRNA synthetase, lose their mitochondrial DNA, rapidly becoming rho–. As a result, these strains are unable to grow on non-fermentable carbon sources even if a complementing gene is introduced into the strain. Therefore, in a haploid strain having a defect in, for example, the yeast mitochondrial methionyl-tRNA synthetase gene (e.g., a gene disruption with a cosegregating selectable marker constructed as indicated above), the haploid strain can be crossed with a rho$^+$ strain having a wild-type mitochondrial methionyl-tRNA synthetase gene to restore the mitochondrial DNA. The resulting rho$^+$ diploid can then be transformed with a plasmid which encodes the wild-type yeast mitochondrial methionyl-tRNA synthetase (i.e., a maintenance plasmid) and a second selectable marker. Following sporulation, progeny spores which carry the defective mitochondrial MetRS, identified by the presence of the cosegregating selectable marker, and the maintenance plasmid, identified by the presence of the second selectable marker, and which are rho$^+$, can be isolated (e.g., by tetrad analysis). Strains constructed in this manner would be suitable for complementation assays using the mycobacterial aminoacyl-tRNA synthetases.

For instance, a plasmid encoding a mycobacterial methionyl-tRNA synthetase gene can be introduced into such a strain on a second plasmid having a third selectable marker. As indicated above, the maintenance plasmid can be selected against (e.g., where the selectable marker is URA3, selection on 5-fluoroorotic acid leads to loss of the maintenance plasmid), and complementation by the mycobacterial gene can be monitored on a non-fermentable carbon source.

In another embodiment, a mitochondrial methionyl-tRNA synthetase gene disruption with a cosegregating selectable marker can be constructed in diploid rho$^+$ strain (see e.g., Edwards, H. and P. Schimmel, Cell, 51:643–649 (1987)). A plasmid encoding a mycobacterial methionyl-tRNA synthetase gene is introduced on a plasmid having a second selectable marker. Sporulation of a resulting diploid yields two progeny spores carrying the yeast mitochondrial methionyl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the mycobacterial gene on the introduced plasmid is indicated by growth on non-fermentable carbon sources of spores carrying the disrupted methionyl-tRNA synthetase gene.

In the case of a mitochondrial tester strain, the mycobacterial methionyl-tRNA synthetase can be imported into mitochondria to achieve complementation of the mitochondrial defect. When it is necessary to achieve import or desirable to improve the efficiency of import of the mycobacterial methionyl-tRNA synthetase in the non-mycobacterial host cell, a gene fusion can be constructed using a sequence encoding a mitochondrial targeting sequence which functions in the host cell. For example, a mitochondrial targeting sequence can be introduced at the amino-terminal end of the mycobacterial methionyl-tRNA synthetase. In one embodiment in yeast, the mycobacterial MetRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus et al., J. Biol. Chem., 263:13097 (1988)). Expression of the construct yields a fusion protein with an N-terminally located cytochrome oxidase IV targeting signal joined to the mycobacterial MetRS protein.

If the construction methods described here are not successful initially, one or more natural or synthetic mycobacterial or other (e.g., procaryotic, such as a bacterial, or eukaryotic, such as a mammalian or fungal) tRNA gene(s) can be introduced into the host cell to provide one or more cognate tRNAs for the mycobacterial aaRS. The tRNA genes of many species have been cloned and sequenced (Steinberg, S., Misch, A. and M. Sprinzl, "Compilation of tRNA sequences and sequences of tRNA genes", Nucleic Acids Res. 21:3011–3015 (1993)). A method for constructing a strain of Streptomyces lividans in which an essential tRNA gene has been inactivated in the chromosome, and the gene is instead maintained on a plasmid, has been described (Cohen, S. N., WO 94/08033 (1994)).

Use of Tester Strains

To assess the inhibitory effect of a substance on a tester strain, the cells are maintained under conditions suitable for complementation of the host cell defect, under which complementation of the host cell defect is dependent upon the test gene (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired. For example, a substance to be tested can be administered to tester cells maintained under assay conditions, and the viability or growth of the tester cells in the presence of the substance can be compared with that of tester cells maintained under the same conditions in the absence of the substance. If it is determined that the substance inhibits growth of the tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous mycobacterial aminoacyl-tRNA synthetase gene present in the tester strain (i.e., the "test gene"), can serve as control strains. These control strains comprise a "control gene" which is an aminoacyl-tRNA synthetase gene other than the heterologous mycobacterial aaRS gene present in the tester strain (i.e., an aaRS gene from a different species, such as a heterologous mycobacterial species or non-mycobacterial (procaryotic or eukaryotic) species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, a cell which is a cell of the same species as the host cell used to construct the tester strain, and which further comprises a control aaRS gene, is selected as a control. For example, the control gene can be a wild-type aaRS gene from the control strain species which encodes an aaRS specific for the same amino acid as the aaRS encoded by the test gene. Such a cell can be used when, for example, the substance or compound to be tested does not significantly affect growth of the control strain under the assay conditions. For example, where an *E. coli* host is used to construct a tester strain having an *M. tuberculosis* aaRS gene, an *E. coli* strain having a wild-type *E. coli* control gene can be used as a control strain. As another example, if a yeast host cell having a defect in a mitochondrial aaRS gene is used to construct the tester strain, a yeast strain comprising the wild type mitochondrial gene can be used as a control strain.

In another embodiment, the control strain can be a strain distinct from the tester strain, which is constructed in a manner which generally parallels that of the tester strain comprising the test gene, such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene", which, as indicated above, is an aaRS gene other than the test gene (i.e., an aaRS gene from a different species, such as a heterologous mycobacterial species or non-mycobacterial (procaryotic or eukaryotic) species). Furthermore, the control gene, which can be cytoplasmic or mitochondrial, encodes an aaRS specific for the same amino acid (e.g., a methionyl-tRNA synthetase) as the test gene (e.g., a methionyl-tRNA synthetase).

Preferably, the control gene is selected from a species which is a host for the mycobacterial pathogen from which the test gene is derived, permitting the identification of specific inhibitors which selectively inhibit the mycobacterial aaRS (e.g., human control gene for an *M. tuberculosis* test gene; a bovine control gene for an *M. bovis* test gene). Alternatively, because the eukaryotic aminoacyl-tRNA synthetases are generally more closely related to each other than to procaryotic aminoacyl-tRNA synthetases, a control gene from another eukaryote (e.g., a different mammalian species) can be used in lieu of one selected from the host species (e.g., a bovine control gene for an *M. tuberculosis* test gene).

For example, a strain isogenic with a tester strain, except for the substitution of a human control gene, can serve as a control strain. Such a control strain can be constructed using the same methods and the same host cell used to construct the tester strain, with the exception that a human control gene is introduced into the host cell in lieu of the heterologous mycobacterial aaRS gene present in the tester.

Under the conditions of this assay, growth or viability of the control strain is dependent upon the control aaRS gene, which complements the host cell aaRS defect in the control strain. Specific inhibition by a substance can be determined by comparing the viability or growth of the tester strain and control strain in the presence of the substance.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an *E. coli* host is used to construct a tester strain comprising an *M. tuberculosis* test gene, an *E. coli* strain comprising a wild-type *E. coli* aaRS gene can be used as a comparison control strain. In another embodiment, "parental-type" cells (e.g., parent host cells or a similar strain) are used as comparison controls. For example, the parent host cells of the tester strain can serve as a comparison control strain for the tester strain. Where the tester strain and the control strain have the same parent, a single strain can be used as the comparison control strain for both tester and control strains.

For example, a parent host cell from which the tester and control strains were both constructed (e.g., by inactivation and replacement of the wild type host aaRS gene) can be used as a comparison control strain. This comparison control strain contains a wild type version of the aaRS gene which is inactivated in the tester and control strains, and the viability or growth of this comparison control strain is dependent upon the wild type aaRS under the conditions of the assay. Specific inhibition of the heterologous mycobacterial aaRS encoded by the test gene (or a step in the expression of the mycobacterial gene) is indicated if, after administering the substance to the tester strain, growth of the tester strain is reduced as compared with an appropriate comparison control strain, and growth of the control strain is not reduced, or is relatively less reduced, as compared with its appropriate comparison control strain.

Testing for Antibiotic Resistance to tRNA Synthetase Inhibitors

Mutation of a drug target can reduce the effectiveness of antimicrobial or antibiotic agents, and can confer drug resistance. Thus, mutation of a target mycobacterial aminoacyl-tRNA synthetase, such as a mycobacterial MetRS, could reduce the effectiveness of an inhibitor of aaRS activity. To test for mutations that confer resistance to an inhibitor (e.g., an inhibitor of MetRS activity, including such an inhibitor having antimicrobial activity) a variety of approaches can be used. Mutant mycobacterial aaRS genes can be obtained, for example, by isolation of a mutant gene, or by preparing an individual mutant gene or an expression library of mutant mycobacterial aaRS genes, such as a library of mutants of a mycobacterial MetRS gene. The mutant gene or gene library can be introduced into suitable host cells for screening for resistance to a compound.

An isolated mycobacterial tRNA synthetase gene, such as an *M. tuberculosis* MetRS gene, can be mutagenized by any suitable method including, but not limited to, cassette mutagenesis, PCR mutagenesis (e.g., the fidelity of PCR replication can be reduced to induce mutation by varying $Mg^{2+}$ concentration, increasing the number of amplification cycles, altering temperatures for annealing and elongation, to yield random mutants), or chemical mutagenesis (e.g., nitrosoguanidine, ethylmethane sulfonate (EMS), hydroxylamine) of the entire gene or a portion thereof. The mutagenesis products can be used to construct an expression library of mutant genes (e.g., by inserting the gene into an expression vector, or replacing a portion of an expression vector comprising the wild-type gene with mutant fragments) which is introduced into a host cell.

In one embodiment, if the inhibitor is known to inhibit the host cell (e.g., *E. coli*, yeast, *Bacillus subtilis*, another mycobacterial species) aminoacyl-tRNA synthetase for the same amino acid, the mutant mycobacterial genes can be introduced into the wild-type host and the resulting cells can be exposed to drug to assess resistance.

In another embodiment, the procedures described above relating to tester strains are used in the method to identify mutants resistant to inhibitor. Introduction of the heterologous mycobacterial mutant aaRS gene(s) (i.e., mutant test gene(s)) into a host cell is carried out as described above for the production of tester strains. For example, the library can be introduced into a host cell having a defect in the endogenous gene encoding MetRS. The metG null strain of *E. coli* designated MN9261/pRMS615 is available as a host for transformation (see Kim et al., *Proc. Natl. Acad. Sci. USA* 90: 10046–10050 (1993), describing a strain which carries a null allele of metG and a temperature sensitive maintenance plasmid, carrying a wild type metG allele (encoding *E. coli* MetRS) and having a temperature sensitive replicon which causes loss of the maintenance plasmid at the nonpermissive temperature).

Active, drug-resistant mutants are then identified by a selection process in which cells containing mutant genes encoding active aaRS are identified, and the effect of an inhibitor upon aaRS activity is assessed. Cells are maintained under conditions suitable for expression of the mutated gene, and cells containing an active mutant aaRS (e.g., active recombinant *M. tuberculosis* MetRS) are identified by complementation of the host cell defect. Where complementation occurs, aach resulting transformant is, in essence, a tester strain comprising a mutant test gene. Cells containing active mutant aaRS as determined by complementation of the host cell defect are then exposed to inhibitor, and the effect of inhibitor on cell growth or viability is assessed to determine whether the active mutant aaRS further confers resistance to inhibitor.

In the case of the metG null strain, complementation by the mycobacterial gene is indicated by growth at the nonpermissive temperature at which the maintenance plasmid is lost. Cells which survive loss of the maintenance plasmid due to the presence of the complementing mutant gene are then challenged with inhibitor to assess resistance.

Resistance can be assessed by comparison to a suitable control by methods analogous to those described above for determining inhibition and/or the specificity of inhibition of a substance in tester cells. For example, the relative effects of an inhibitor upon a tester strain comprising the mutant test gene and upon a tester strain differing only in that it contains the test gene lacking the mutation, can be assessed by comparing the viability or growth of cells which are dependent upon either the test gene or mutant test gene for growth under conditions suitable for complementation of the host cell defect. For instance, the effect of inhibitor on the protein encoded by the test gene lacking the mutation can be determined by comparing the growth of cells containing the test gene in the presence of drug to the growth of such cells in the absence of drug, and the effect of inhibitor on the protein encoded by a mutant test gene can be determined by comparing growth of cells containing the mutant test gene in the presence of drug to the growth of such cells in the absence of drug. A decrease in the inhibitory effect on growth of cells carrying the mutant test gene as compared to the inhibitory effect against cells carrying the test gene lacking the mutation is indicative of resistance.

Cells containing a complementing mutant test gene which further confers resistance to an inhibitor can be used to identify derivatives of the inhibitor with improved antimicrobial effect, which circumvent resistance. Such cells can also be used to identify additional inhibitors having inhibitory activity against the active mutant aaRS encoded by the mutant test gene.

In another embodiment, a naturally occurring mutant mycobacterial aaRS gene, which confers resistance to an inhibitor upon a mycobacterial cell, can be isolated from the mycobacterium using nucleic acids of the present invention as probes. The cloned gene can then be introduced into a host cell as described for the production of tester strains. Tester cells comprising the mutant test gene which confers resistance, and complements the host defect, can be used as described herein to identify additional inhibitors having reduced susceptibility to the resistance mutation or derivatives of the inhibitor with improved inhibitory activity.

Vectors carrying mutant genes which confer resistance to inhibitor can be recovered and the insert analyzed to locate and identify the mutation by standard techniques, such as DNA sequence analysis, to yield additional information regarding the nature of mutations capable of conferring resistance to selected inhibitors. Mutant proteins can also be expressed and purified for further characterization by in vitro kinetic and binding assays.

Applications in Biochemistry

The mycobacterial methionyl-tRNA synthetase or stable subdomains of the protein can be used in a method to separate methionine from a mixture of methionine and other compounds such as other amino acids, or to specifically isolate L-methionine from D-methionine. The tRNA synthetase can be chemically attached to a solid support material packed in a column or other suitable container. Alternatively, a fusion protein such as a GST-Met tRNA synthetase fusion or a His tail-Met tRNA synthetase fusion permits attachment to a suitable solid support which binds the GST portion or His tail portion of the fusion protein, respectively. The mixture of methionine and other compounds can be loaded onto the column under conditions in which methionine binds to the tRNA synthetase enzyme, while other compounds present in the mixture flow through the column. In a later step, methionine can be released from the enzyme by changing the conditions in the column, such as washing with a solution of high ionic strength to elute L-methionine.

In a similar manner, the mycobacterial methionyl-tRNA synthetase can be used in a method to isolate tRNA that specifically recognizes the tRNA synthetase.

The mycobacterial methionyl-tRNA synthetase can be used in the quantitative determination of methionine by its conversion to methionyl hydroxamate. An example of an appropriate assay is illustrated by the following series of reactions:

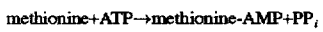

(in the presence of excess pyrophosphatase and ATP at pH 7.5, where pyrophosphatase catalyzes the conversion of the product inorganic pyrophospate ($PP_i$) to inorganic orthophospate ($P_i$); ATP is adenosine triphospate; AMP is adenosine monophosphate)

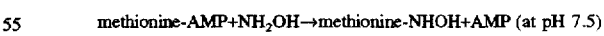

The resulting colored complex can be quantitated by spectrophotometric measurements of absorbance at 540 nm, and compared with a standard curve made using known concentrations of methionine. This assay is based on the reactions described by Stulberg and Novelli, *Methods in Enzymology* 5:703–707 (1962).

The mycobacterial methionyl-tRNA synthetase can also be used for the quantitative determination of ATP. In the presence of excess methionine, and in the presence of pyrophosphatase to convert the product $PP_i$ to $P_i$, the ATP will be quantitatively converted to AMP and inorganic pyrophosphate by the methionyl-tRNA synthetase.

methionine+ATP→methionyl-AMP+PP$_i$ (in the presence of MetRS)

PP$_i$+H$_2$O→2P$_i$ (in the presence of pyrophosphatase)

P$_i$ can be quantitated by reaction with molybdate, measuring the absorbance at 580 nm and comparing to a standard curve made using known quantities of orthophosphate.

The present invention is more specifically illustrated in the following examples, which are not intended to be limiting in any way.

Example 1

Isolation of a MetRS Gene Fragment by PCR from *M. tuberculosis* and *M. kansasii* Genomic DNA The polymerase chain reaction (PCR) was used to obtain a Met tRNA synthetase gene fragment from *M. tuberculosis* (Erdman H37RV; Oatway, W. H., et al., *J. Infect. Dis.* 59:306–325 (1936)) and *M. kansasii* genomic DNA. The PCR primers were designed by aligning polypeptide sequences obtained from Genbank for different species of Met tRNA synthetase (*Bacillus stearothermophilus*, Tetrahymena (mitochondria), *T. thermophilus, E. coli, S. cerevisiae* (cytoplasmic)) using the PILEUP program (Table 1; Needleman and Wunsch, *J. Mol. Biol.* 48:443–453 (1970)). A total of four degenerate primers (Kiyo-12 (SEQ ID NO:10) and -13 (SEQ ID NO:11) for forward and Kiyo-14 (SEQ ID NO:12) and -15 (SEQ ID NO:13) for reverse; see Table 1), which are directed at two Met tRNA synthetase sequence motifs, were synthesized and used for PCR using a thermocycler. Either *M. tuberculosis* (or *M. kansasii*) genomic DNA (15 ng) were combined with 100 pmoles of each forward and reverse primer and mixed with Taq polymerase (1.5 units, Perkin-Elmer) in 50 μl of 10 mM Tris-HCl (tris(hydroxymethyl)aminomethane hydrochloride), pH 8.3, 1.5 mM $MgCl_2$, 50 mM KCl, 0.1 mg/ml gelatin, and 50 μM of each dNTP. The cycles for denaturation (94° C., 30"), annealing (55° C., 30") and extension (72° C., 90") were repeated 35 times (30 times for *M. kansasii*). The PCR products were analyzed by gel electrophoresis and then purified by Gene Clean (Bio 101). The *M. kansasii* purified DNA fragment was cloned into the SmaI site of pTZ19R (Pharmacia), the *M. tuberculosis* fragment was cloned into the EcoRI site of pBSKS+, and the constructs were used to transform *E. coli* strain XL1-Blue (Stratagene) and *E. coli* DH5α, respectively. The plasmid DNA was isolated using either Wizard miniprep kits (Promega) or Qiagen Midi-prep kits. The *M. tuberculosis* and *M. kansasii* Met tRNA synthetase PCR fragments were sequenced using a Sequenase 7-Deaza-dGTP DNA sequencing kit (Version 2.0 T7 DNA Polymerase, U.S. Biochemical). Standard protocols were used with the exception that 10% dimethylsulfoxide (DMSO) was included in all the reaction mixtures to facilitate the sequencing of DNA with a high G-C content.

Example 2

Southern Hybridization

Genomic DNA from *M. tuberculosis*, BCG (M. bovis bacillus Calmette-Guérin) and *E. coli* was restriction digested, separated on an agarose gel by electrophoresis, denatured and transferred to a membrane (Hybond N, Amersham). The probe DNA was a (denatured) [$^{32}$P]-labeled 599 basepair fragment, comprising the amplified *M. kansasii* sequence (Positions 589–599 (GGGATCCTCT) are vector-derived residues), which was released from the pTZ19R vector into which it had been cloned (SEQ ID NO:3). This fragment had been generated from *M. kansasii* DNA by PCR using primers designed to be homologous to well-conserved regions in the MetRS gene, based on known sequences of MetRS genes of other unrelated organisms.

In the prehybridization step, the membrane was incubated at 68° C. for 2 h in 5×Denhardt's solution, 5×SSC, 0.5% SDS and 2 mM EDTA. The hybridization solution was the same except for the addition of probe DNA. Incubation was at 68° C. overnight. Following hybridization, the membrane was washed twice with 2×SSC, 0.1% SDS for 1 h at room temperature, then twice with 0.5×SSC, 0.1% SDS for 1 h at 65° C.

Autoradiography of the membrane revealed that the probe had hybridized to a 3 kb band in the lanes containing the DNA from *M. tuberculosis* and from BCG, but not to the DNA from *E. coli.*

Example 3

Screening of *M. tuberculosis* Genomic Library

The *M. kansasii* PCR fragment was obtained earlier than the corresponding *M. tuberculosis* PCR fragment. Thus, the former was used as a probe to screen a λgt11 *M. tuberculosis* genomic library which was provided by Professor R. Young, Whitehead Institute, Cambridge (Young, R., et al., *Proc. Natl. Acad. Sci. USA* 82:2583–2587 (1985)). The *M. kansasii* PCR fragment was recovered by EcoRI and XbaI digestion from the derivative of pTZ19R (Pharmacia) into which the original PCR fragment had been cloned (Example 1), and 50 ng of the EcoRI-XbaI fragment were radiolabelled using the Random Primer DNA Labelling Kit (Boehringer-Mannheim Biochemicals, Inc.) according to the commercial protocol. The labeled PCR fragment was purified using a Nap-5 column (Pharmacia). The typical yield was about 30,000 cpm/ml.

The λgt11 library was amplified in 250 ml LB (Luria Broth) and spread on plates (25×25 cm) to obtain about 100,000 plaques/plate. The plaques were transferred to duplicate Gene Screen, Hybridization Transfer nylon membranes (Dupont) and the DNA denatured by soaking the membranes in 0.2N NaOH, 1.5M NaCl for 5 min followed by neutralization in 0.4M Tris, 2×SSC (1×SSC is 150 mM NaCl, 15 mM sodium citrate, pH 7.0) for 5 min. The membranes were air dried for 30 min and then baked at 80° C. for one hour. The pre-hybridization was carried out by incubating the membranes in 50 ml of hybridization solution (500 mM $NaH_2PO_4(H_2O)$, 5% dextran sulfate, 7% SDS (sodium dodecyl sulfate), 1 mM EDTA (ethylenediamine tetraacetic acid), 100 μg/ml salmon sperm DNA, 50% formamide, 250 mM NaCl) for a minimum of one hour at 37° C. The radio-labelled *M. kansasii* probe was denatured at 90° C. for 5 min and then a $1.5\times10^7$ CPM aliquot of probe was added to 50 ml of hybridization solution and incubated with the membrane overnight at 37° C. The membrane was washed two times in 2×SSC, 0.1% SDS at room temperature for 10 min each, and then two times in 0.5×SSC, 0.1% SDS at 65° C. for one hour each. The membranes were dried at room temperature for 15 min and then analyzed by autoradiography.

Seven positive plaques were selected from the duplicate membranes and five were successfully verified in two subsequent screens. The phage DNA was purified using the Wizard Lambda Preps DNA Purification System (Promega).

The λgt11 was digested with EcoRI producing a 6 kilobase (kb) insert which was cloned into the EcoRI site of PBSKS+ (Stratagene) and used to transform *E. coli* (DH5α). Plasmids designated pSH101A and pSH101B were recovered with the gene inserted in each orientation.

Plasmid pSH101A in *E. coli* DH5α was deposited in accordance with the provisions of the Budapest Treaty at the American Type Culture Collection (ATCC), 12301 Parklawn Drive, Rockville, Md. 20852, U.S.A. on Mar. 27, 1997, and assigned Accession Number ATCC 98376.

Example 4

Sequencing and Expression of *M. tuberculosis* Met tRNA Synthetase

The sequence of the 6 kb fragment was determined in a sequential manner initially using primers based on the λgt11 vector sequence. Internal sequencing primers were designed based on the *M. tuberculosis* PCR fragment. The sequencing procedure was carried out as described previously for the PCR fragment characterization. Random data base searches were carried out using the BLAST algorithm (Basic Local Alignment Search Tool; Gish et al., *Nature Genetics* 3:266–272 (1993); Altschul et al., *J. Mol. Biol.* 215:403–410 (1990)).

The nucleotide sequence determined for the for *M. tuberculosis* methionyl-tRNA synthetase gene is shown in SEQ ID NO:1. The sequence contains an open reading frame (ORF) which encodes a polypeptide of 521 amino acids. Random data base searches (National Center for Biotechnology Information (NCBI)) were carried out on the amino acid sequence of *M. tuberculosis* Met tRNA synthetase (translating from the GTC at position 1 in SEQ ID NO: 1) using the BLAST (Basic Local Alignment Search Tool) algorithm (Altschul, S. F., et al., *J. Mol. Biol.*, 215:403–410 (1990); Gish, W., and D. J. States, *Nature Genetics*, 3:266–272 (1993)) to identify amino acid sequences in the database which are homologous to the sequence determined for *M. tuberculosis* Met tRNA synthetase. A further comparison of the sequence determined for *M. tuberculosis* Met tRNA synthetase with the Met tRNA synthetase sequences identified in these searches was performed using the multiple sequence alignment program from the DNA star package. In particular, percent similarity and percent divergence were determined using the Jotun-Hein method and the Structural residue weight table. The percent similarity between the predicted 521-amino acid sequence of *M. tuberculosis* Met tRNA synthetase the and methionyl-tRNA synthetases from *Bacillus stearothermophilus* and *Thermus thermophilus* was found to be 37.0% and 35.0%, respectively. Other sequences were even less related.

A 1.7 kb fragment comprising the gene for *M. tuberculosis* Met tRNA synthetase was cloned into three expression vectors: Bluescript®SK+ (Stratagene), pGEX-4T-2 (Pharmacia) and pET-15b (Novagen). To aid in cloning, the ends of the full-length gene were engineered by PCR using specifically designed PCR primers and pSH101A as DNA template. For insertion into Bluescript®II SK+, the 5' PCR primer introduced a BamHI end (5'-GATCC) on the coding strand followed by a single G residue (to maintain the reading frame) immediately prior to the initiator codon of the Met tRNA synthetase gene (see SEQ ID NO:1, GTC at position 1), which was altered in the primer sequence to an ATG for expression in *E. coli*. The 3' PCR primer, having the sequence 5'-CCGGAATTCTTAACGATTCCGGGTTTTATCCCGTCGCCAC-3' (SEQ ID NO:4), introduced an EcoRI end to facilitate cloning downstream of the coding sequence. The PCR product was inserted into BamHI-EcoRI digested Bluescript®II SK+. The central 1.5 kb of the resulting clone was excised by BsaAI and RsrII digestion and was replaced with the corresponding fragment of the cloned genomic DNA present in pSH101A. The resulting plasmid, designated pSLM101, encodes a β-Gal-Met tRNA synthetase fusion protein, comprising the complete Met tRNA synthetase protein sequence (See SEQ ID NO:2) and 33 additional amino acids at the N-terminus. Expression of protein is induced by IPTG, but some protein is expressed even in the absence of induction.

For the in-frame insertion into pGEX-4T-2, the 5' PCR primer introduced a BamHI end (5'-GATCC) on the coding strand followed by 3 bases (GCG) immediately prior to the initiator codon of the Met tRNA synthetase gene (GTC at position 1 of SEQ ID NO:1), which was altered in the primer sequence to an ATG for expression in *E. coli*. The 3' PCR primer, which was the same as that used to construct pSLM101, introduced an EcoRI end downstream of the coding sequence). The PCR product was inserted into BamHI-EcoRI digested pGEX-4T-2. Again, the central 1.5 kb of the resulting clone was excised by BsaAI and RsrII digestion and was replaced with the corresponding fragment of the cloned genomic DNA present in pSH101A. The resulting plasmid, designated pSLM201, encodes a GST-fusion protein, comprising the complete Met tRNA synthetase sequence.

For the in-frame insertion into pET-15b, the 5' PCR primer introduced a BamHI end (5'-GATCC) on the coding strand followed by a single G residue immediately prior to the initiator codon of the Met tRNA synthetase gene (GTC at position 1 of SEQ ID NO:1), which was altered in the primer sequence to an ATG for expression in *E. coli*. The 3' PCR primer, having the sequence 5'-CCGGATCCCGTACGATTCCGGGTTTTATCCCGTCGCCAC-3' (SEQ ID NO:5), introduced a BamHI end 3' to the coding sequence. The PCR product was inserted into BamHI digested pET-15b. Again, the central 1.5 kb of the resulting clone was excised by BsaAI and RsrII digestion and was replaced with the cloned genomic DNA present in pSH101A. The resulting plasmid, designated pSLM301, encodes a fusion protein, comprising the His-Tag and thrombin cleavage sites from the pET-15b vector, and the complete Met tRNA synthetase sequence.

The pSLM101 and pSLM201 plasmids were used to transform a DH5α strain of *E.coli*, while the pSLM301 plasmid which, requires T7 RNA polymerase for expression, was used to transform *E.coli* strain BL21 (DE3) (Stratagene). The transformed cells were grown overnight in 1.0 ml cultures of LB with 50 μg/ml ampicillin (Ap), resulting in an $A_{600}$ of 2–3. The cultures were used to inoculate 5 ml of LB (50 μg Ap/ml) cultures which were grown at 37° C. for 2–3 hours until the $A_{600}$ reached 0.6. Protein expression was induced by the addition of IPTG (isopropyl-β-D-thiogalactopyranoside) to a final concentration of 1 mM. The induction period was one hour for pSLM301, two hours for pSLM201, and four hours for pSLM101. The cells were recovered by centrifugation, sonicated, and the crude cell extracts analyzed by SDS (sodium dodecylsulfate) polyacrylamide gel electrophoresis on a 10% polyacrylamide gel. Coomassie staining of the gels revealed that the protein was expressed using all three vector constructions.

Example 5

Purification and Aminoacylation Activity of the *M. tuberculosis* GST-Met tRNA Synthetase A 50 ml LB culture (plus 50 μg/ml Ap) of *E.coli* harboring the pSLM201 plasmid was grown to an $A_{600}$ of 0.6 and protein expression was induced by addition of IPTG to 0.1 mM and continued growth for 2 hours. The cells were recovered by centrifugation in a Sorvall Super 21 (Dupont) and stored at −20° C. until protein purification.

The cells were suspended in 50 ml of 1×PBS (140 mM NaCl, 2.7 mM KCl, 10 mM Na$_2$HPO$_4$, 1.8 mM KH$_2$PO$_4$, pH 7.3) and lysed by sonication at 75%/1 sec power using a Sonicator Ultrasonic Processor (Heat Systems) for about 2 min until the the solution cleared. A 50 μl aliquot of 20% Triton X-100 in 1×PBS was added followed by gentle mixing at 4° C. for 30 min. The lysis mixture was centrifuged at 10,000 rpm for 10 min at 4° C. The pellet debris was discarded and the supernatant recovered to be further purified by column chromatography.

Approximately 3 ml of glutathione agarose resin (14 mmol/ml, Sigma) was pre-equilibrated with 20 ml 1×PBS in a 1×4 cm Bio-Rad Econo-column. Five ml of the cell extract was loaded and the column washed with 30 ml 1×PBS. The protein was eluted in 10 ml of 10 mM glutathione, 50 mM Tris, pH 8.0. The protein was identified by SDS-PAGE gel electrophoresis on a 10% polyacrylamide gel by the predicted molecular weight of the protein in the prominent band and by the absence of the band in cell extracts from a control strain.

Aminoacylation reactions were based on those described in Martinis and Schimmel, *Proc. Natl. Acad. Sci. USA* 89:65–69 (1992). Reactions were carried out in 20 mM Hepes, pH 7.5, 100 μM Na$_2$EDTA, 150 mM NH$_4$Cl, 100 μg of bovine serum albumin/ml, 4 mM ATP, 10 mM MgCl$_2$, 20 μM methionine, 0.2 mCi [$^{35}$S] methionine/ml (1 Ci=37 GBq, Amersham) and 2 μM tRNA$^{fMet}$ (Sigma). The reaction was quenched by placing a 10 μl aliquot on a 2.3-cm Whatman 3MM filter pad, which was pre-soaked in 10% (v/v) trichloroacetic acid/2 μM methionine. The pads were slowly shaken on ice in 500 ml of this wash solution with four changes over a time period of 2 hours. The pads were incubated subsequently in 200 ml of 95% ethanol, 100 ml of ether and then dried under a heat lamp. The filter pads were combined with 5 ml Betafluor (National Diagnostics) and the aminoacylated tRNA$^{fMet}$ quantitated by scintillation counting in a Packard 1600 TR. Results were compared with those obtained from experiments performed in parallel using *E.coli* methionyl-tRNA synthetase that had been purified by a DEAE column. The results are presented in FIG. 1.

Example 6

Yeast Strains and Construction of Mitochondrial Expression Vectors

Standard methods for yeast propagation and transformation were used (see e.g., Ausubel, F. M., et al., *Current Protocols in Molecular Biology*, Greene Publishing Associates and John Wiley & Sons, Inc., (1993); Rose et al., *Methods in Yeast Genetics*, (Cold Spring Harbor Laboratory Press: Cold Spring Harbor, N.Y.) 1990). Standard molecular biology methods were used (Ausubel, et al., 1993). Enzymes were purchased from New England Biolabs. Plasmid DNA was isolated using Qiagen columns (Qiagen, Chatsworth, Calif.).

The rho° strains QBY51 and QBY52 were obtained by growing QBY19 (MATa ade6 lys1) and QBY20 (MATα ade6 lys1) in YEPD (yeast extract, peptone, dextrose medium) containing 10 μg/ml of ethidium bromide (Sigma) to induce loss of mitochondrial DNA.

The mitochondrial methionyl-tRNA synthetase mutant strain used in this study is the point mutation strain QBY42 (C122/U2) MATα ura3-1, msm1-1 (Tzagoloff, A., et al., *Eur. J. Biochem.*, 179:365–371 (1989)). Strain QBY171 (D273-10B) MATα mal rho$^+$ (ATCC #24657), which is similar to the parental MSM1 strain (i.e., D273-10B/A1) of the mitochondrial point mutant strain, was used as a positive control.

Disruption strain QBY43 (aW303∇msm1) (MATa ade2-1 his3-11,15 leu2-3,112 ura3-1 trp1-1 msm1::HIS3; see Tzagoloff, A., et al., *Eur. J. Biochem.*, 179:365–371 (1989)) was also used in these studies. Strains QBY3 (EY699) ((MATa ade2-1 his3-11,15 leu2-3,112 ura3-1 trp1-63 can1-100 Gal$^+$) (Elion, E. A. et al., *Proc. Natl. Acad. Sci. USA*, 88:9392–9396 (1991)) and QBY4 (EY722) (MATα ade2-1 his3-11,15 leu2-3,112 ura3-1 trp1-1 can1-100 Gal$^+$) were used also as MSM1 positive controls in the studies described. QBY4 is nearly isogenic with the parent of the disruption strain, differing only at the MAP locus.

pQB111 and pQB136

The presequence from the cytochrome oxidase IV was used in the mitochondrial import vectors pQB111 and pQB136. This sequence has been used to allow import of several heterologous proteins in the mitochondria (Hurt, E. C., et al., *EMBO J.* 3:3149–3156 (1984); Pinkham, J., et al., *Mol. and Cell. Biol.* 14:4643–4652, (1994)).

In order to construct pQB111, an SphI-XbaI fragment bearing the ADH1 promoter and 22 of the 25 amino acids of COXIV (cytochrome oxidase IV) presequence was excised from plasmid pMC4 (obtained from J. Pinkham, University of Massachusetts, Amherst) (Bibus, C. R., et al., *J. Biol. Chem.* 263:13097–13102 (1988); Hurt., E. C., et al., *J. Biol. Chem.* 262:1420–1424 (1987)) and cloned into the SphI and XbaI sites of YEplac195 (also referred to as pQB42), (Sugino, A., and Gietz, R. D. *Gene* 74:527–534 (1988)) to form pQB111.

Figure 2A:
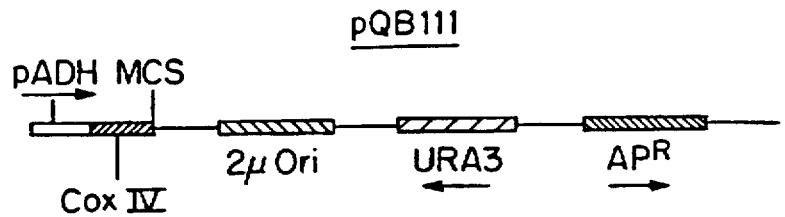
FIGS. 2A–2B are schematic diagram of the structures of shuttle vectors pQB111 and pQB136 (Example 6). Genes, such as *M. tuberculosis* methionyl-tRNA synthetase, can be inserted into these constructs, which permit expression in *S. cerevisiae*, and include a presequence for targeting the protein encoded by the inserted gene to mitochondria. (The circular plasmids are presented in linear form; pADH, alcohol dehydrogenase (ADH1) gene promoter; CoxIV, sequence encoding from 1–22 (pQB111) or 1–25 (pQB136) amino acids of the cytochrome oxidase IV presequence; MCS, multiple cloning site; 2μ Ori, 2 micron origin of replication; URA3, selectable marker; AP$^R$, ampicillin resistance).
Figure 2B:
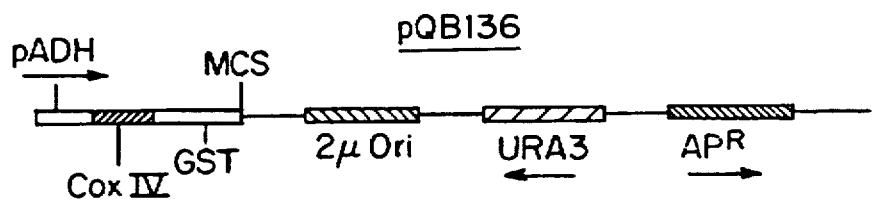

Plasmid pQB136 is a derivative of pQB111 which allows construction of GST fusion proteins targeted to mitochondria. PCR was used to amplify the GST gene from pGEX-4T-2 (Pharmacia) using the following primers: 5' GCGC <u>TCTAGA</u>TATCTGCTT <u>ATG</u>TCCCCTATACTAGGTTATTGG 3' (SEQ ID NO:6), and 5' GG<u>GGTACC</u>TCACGATGCGGCCGCTCGAG 3' (SEQ ID NO:7) (The ATG underlined in the 5'-primer is the start site of GST; the bases in boldface specify amino acids 22–25 of the COXIV presequence). The 5' primer introduced an XbaI site (underlined), which when fused to the XbaI site in plasmid pQB111, restores the entire (25 amino acid residue) presequence of COXIV. The 3' primer introduces a KpnI site (underlined) downstream of the GST stop codon. A schematic diagram of the two plasmids is shown in FIGS. 2A–2B.

pQB150 and pQB151

Plasmid pQB150, bearing the methionyl-tRNA synthetase gene from *M. tuberculosis* was made by cloning the 1.7 kb BamHI fragment from pSLM101 (see Example 4) into the BamHI site of pQB111. Plasmid pQB151 expressing the *M. tuberculosis* gene as a GST fusion protein was made in a similar way using pQB136 as the vector for insertion.

pQB316

Plasmid pQB116 is a derivative of plasmid pQB111 allowing mitochondrial targeting of the methionyl-tRNA synthetase of *E.coli*. The source of the *E.coli* gene is plasmid pJB104 (Kim, S. and Schimmel, P., *J. Biol. Chem.* 267:15563–15567 (1992)). The gene was excised using AccI (filled-in) and Eco47III and was ligated to pQB111 (XmaI-cut and filled-in).

pQB141 and pQB142

Plasmids pQB141 and pQB142 contain a 2.5 kb KpnI-PstI fragment containing the MSM1 gene promoter and entire MSM1 coding region isolated from plasmid pQB104 (pG72/T1) (Tzagoloff, A., et al., *Eur. J. Biochem.* 179:365–371 (1989)), and cloned into plasmids YCplac33 and YEplac195 (Sugino, A., and Gietz, R. D., *Gene* 74:527–534 (1988)), respectively. In each case, the fragment is inserted into KpnI and PstI sites.

pQB152

Plasmid pQB152 carrying a GST-MSM1 protein fusion was constructed by PCR amplification of the wild type MSM1 gene from plasmid pQB104 (pG72/T1) (Tzagoloff, A., et al., *Eur. J. Biochem.* 179:365–371 (1989)), using the following primers: 5' CCGCTCGAGCGATGCA ATGTCGATCAATTGTGC3' (SEQ ID NO:8) and 5' GG GGTACCCCTTTTTCATGACCTCATATTCG 3' (SEQ ID NO:9). The PCR product was cleaved with XhoI and KpnI and cloned into the XhoI and KpnI sites of pQB136. In subsequent studies pQB152, encoding a GST-MSM1 fusion, was observed to complement msm1-1 and msm1::HIS3 strains on YEPG medium, but did not complement as well as pQB141 or pQB142, which encode MSM1 alone.

Related Mycobacterial Aminoacyl-tRNA Synthetases and Tester Strains

In addition to the gene encoding methionyl-tRNA synthetase described herein, genes encoding leucyl-, seryl-, isoleucyl- and tyrosyl-tRNA synthetases from *M. tuberculosis* have been isolated and sequenced as described in U.S. Ser. No. 08/305,171 (Attorney Docket No. CPI94-06), U.S. Ser. No. 08/305,172 (Attorney Docket No. CPI94-07), U.S. Ser. No. 08/305,765 (Attorney Docket No. CPI94-08) and U.S. Ser. No. 08/305,181 (Attorney Docket No. CPI94-20), respectively, filed concurrently herewith, and the teachings of which are each hereby incorporated by reference in their entirety. These isolated genes are representatives of a broader class of mycobacterial aminoacyl-tRNA synthetase genes, including synthetase genes encoding enzymes specific for each amino acid and derived from various species

TABLE 1

DESIGN OF DEGENERATE PCR PRIMERS

| Species | Polypeptide Sequence (N- → C-terminal)/Degenerate Primer | | | | | | | | |
|---|---|---|---|---|---|---|---|---|---|
| Tmt-M | F | L | T | G | T | D | E | H | G(SEQ ID NO: 14) |
| Bst-M | y | L | T | G | T | D | E | H | G(SEQ ID NO: 15) |
| Scm-M | F | t | T | G | T | D | E | H | G(SEQ ID NO: 16) |
| Kiyo-12 (5'→3') | TWY | CTI | ACI | GGI | ACI | GAY | GAR | CAY | GG |
| Ec-M | F | I | C | a | d | D | a | H | G(SEQ ID NO: 17) |
| Sc-M | F | I | C | G | T | D | E | y | G(SEQ ID NO: 18) |
| Kiyo-13 (5'→3') | TTY | ATI | TGY | GGI | ACI | GAY | GAR | YAY | GG |
| Tmt-M | Y | V | W | F | D | A | L | l | N | Y(SEQ ID NO: 19) |
| Bst-M | Y | V | W | i | D | A | L | a | N | Y(SEQ ID NO: 20) |
| Scm-M | Y | V | W | F | D | A | L | c | N | Y(SEQ ID NO: 21) |
| (5'→3') | TAY | GTI | TGG | WTY | GAY | GCI | CTI | ATI | AAY | TAY |
| Kiyo-14 (3'→5') | ATR | CAI | ACC | WAR | CTR | CGI | GAI | TAI | TTR | ATR |
| Ec-M | Y | V | W | L | D | A | p | I | G | Y(SEQ ID NO: 22) |
| Sc-M | Y | V | W | F | D | A | t | I | G | Y(SEQ ID NO: 23) |
| (5'→3') | TAY | GTI | TGG | YTI | GAY | GCI | MCI | ATY | GGI | TAY |
| Kiyo-15 (3'→5') | ATR | CAI | ACC | RAI | CTR | CGI | KGI | TAR | CCI | ATR |

Degenerate primers were specifically designed to amplify aminoacyl-tRNA synthetase gene fragments by PCR from *M. tuberculosis* or *M. kansasii* genomic DNA, or the DNA of other organisms. Lower case amino acid abbreviations indicate amino acid residues whose codons are not complementary to the corresponding degenerate primer.

All primers (Kiyo-12, SEQ ID NO:10; Kiyo-13, SEQ ID NO:11; Kiyo-14, SEQ ID NO:12; Kiyo-15, SEQ ID NO:13) included an additional 5'-GCGAATTC at the 5' end.

Abbreviations

Amino acids

Standard single letter amino acid codes are used.

Bases

I—inosine
R—A,G
Y—T,C
M—A,C
K—T,G
W—A,T
S—G,C
H—A,T,C
Ec—*E.coli*
Sc—*S. cerevisiae*
Scm—*S. cerevisiae-mitochondrial*
Bst—*B. stearothermophilus*
Tmt—*T. thermophilus* of mycobacteria, each of which gene can be used to express mycobacterial aminoacyl-tRNA synthetase protein, with utilities corresponding to those described herein, and which can be used in the production of tester strains comprising recombinant mycobacterial aminoacyl-tRNA synthetase genes by methods analogous to those described herein. The approaches described herein, including, but not limited to, the approaches to isolate and manipulate the methionyl-, leucyl-, seryl-, isoleucyl- and tyrosyl-tRNA synthetase genes of *M. tuberculosis*, to construct vectors and host strains, to produce and use the enzymes, to produce antibodies, etc., can be applied to other aminoacyl-tRNA synthetases of the genus Mycobacterium.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. An isolated nucleic acid which encodes an aminoacyl-tRNA synthetase of a species of the genus Mycobacterium, wherein said aminoacyl-tRNA synthetase is selected from the group consisting of methionyl-tRNA synthetase, isoleucyl-tRNA synthetase, leucyl-tRNA synthetase, valyl-tRNA synthetase and cysteinyl-tRNA synthetase.

2. An isolated nucleic acid of claim 1, wherein said nucleic acid is a recombinant nucleic acids.

3. An isolated nucleic acid of claim 1, wherein the aminoacyl-tRNA synthetase is a leucyl-tRNA synthetase.

4. An isolated nucleic acid of claim 3, wherein said species is *M. tuberculosis*.

5. An isolated nucleic acid of claim 1, wherein the aminoacyl-tRNA synthetase is a valyl-tRNA synthetase.

6. An isolated nucleic acid of claim 5, wherein said species is *M. tuberculosis*.

7. An isolated nucleic acid of claim 1, wherein the aminoacyl-tRNA synthetase is a cysteinyl-tRNA synthetase.

8. An isolated nucleic acid of claim 7, wherein said species is *M. tuberculosis*.

9. An isolated nucleic acid encoding a methionyl-tRNA synthetase of a species of the genus Mycobacterium.

10. An isolated nucleic acid of claim 9, wherein said nucleic acid is a recombinant nucleic acid.

11. An essentially pure nucleic acid which encodes a mycobacterial methionyl-tRNA synthetase, wherein said nucleic acid hybridizes to DNA having the sequence SEQ ID NO:b 1,its complement, DNA having the sequence SEQ ID NO:3 or its complement, under conditions comprising a) hybridization overnight in 500 mM $NaH_2PO_4(H_2O)$, 5% dextran sulfate, 7% SDS, 1 mM EDTA, 50% formamide, 250 mM NaCl, and 100 µg/ml salmon sperm DNA at 37° C., b) washing twice in 2×SSC, 0.1% SDS for 10 minutes each at room temperature, and c) washing twice in 0.5×SSC, 0.1% SDS for one hour each at 65°.

12. An essentially pure nucleic acid which encodes a mycobacterial methionyl-tRNA synthetase of claim 11, wherein the mycobacterium is *Mycobacterium tuberculosis*.

13. An essentially pure nucleic acid which encodes a mycobacterial methionyl-tRNA synthetase, wherein said nucleic acid hybridizes to DNA having the sequence SEQ ID NO:1, its complement, DNA having the sequence SEQ ID NO:3 or its complement, under conditions comprising a) hybridization overnight in 5×Denhardt's solution, 5×SSC, 0.5% SDS and 2 mM EDTA at 68° C., b) washing twice with 2×SSC, 0.1% SDS for one hour at room temperature, and c) washing twice with 0.5×SSC, 0.1% SDS for one hour at 65°.

14. An essentially pure nucleic acid which encodes a mycobacterial methionyl-tRNA synthetase of claim 13, wherein the mycobacterium is *Mycobacterium tuberculosis*.

15. An isolated nucleic acid which encodes a methionyl-tRNA synthetase of *Mycobacterium tuberculosis*.

16. An isolated nucleic acid of claim 15, wherein said nucleic acid is a recombinant nucleic acid.

17. An essentially pure nucleic acid which encodes a protein comprising a polypeptide having an amino acid sequence corresponding to amino acids 3–521 in SEQ ID NO:2.

18. A nucleic acid vector comprising nucleic acid encoding an aminoacyl-tRNA synthetase of a species of the genus Mycobacterium, wherein said aminoacyl-tRNA synthetase is selected from the group consisting of methionyl-tRNA synthetase, isoleucyl-tRNA synthetase, leucyl-tRNA synthetase, valyl-tRNA synthetase and cysteinyl-tRNA synthetase.

19. A nucleic acid vector of claim 18, wherein the aminoacyl-tRNA synthetase is a leucyl-tRNA synthetase.

20. A nucleic acid vector of claim 19, wherein said species is *M. tuberculosis*.

21. A nucleic acid vector of claim 18, wherein the, wherein the aminoacyl-tRNA synthetase is a valyl-tRNA synthetase.

22. A nucleic acid vector of claim 21, wherein said species is *M. tuberculosis*.

23. A nucleic acid vector of claim 18, wherein the aminoacyl-tRNA synthetase is a cysteinyl-tRNA synthetase.

24. A nucleic acid vector of claim 23, wherein said species is *M. tuberculosis*.

25. A nucleic acid vector comprising nucleic acid encoding a mycobacterial methionyl-tRNA synthetase, wherein said nucleic acid hybridizes to DNA having the sequence SEQ ID NO:1, its complement, DNA having the sequence SEQ ID NO:3 or its complement, under conditions comprising a) hybridization overnight in 500 mM $NaH_2PO_4$ ($H_2O$), 5% dextran sulfate, 7% SDS, 1 mM EDTA, 50% formamide, 250 mM NaCl, and 100 µg/ml salmon sperm DNA at 37° C., b) washing twice in 2×SSC, 0.1% SDS for 10 minutes each at room temperature, and c) washing twice in 0.5×SSC, 0.1% SDS for one hour each at 65°.

26. A nucleic acid vector comprising nucleic acid encoding a mycobacterial methionyl-tRNA synthetase of claim 25, wherein the mycobacterium is *Mycobacterium tuberculosis*.

27. A nucleic acid vector comprising nucleic acid encoding a mycobacterial methionyl-tRNA synthetase, wherein said nucleic acid hybridizes to DNA having the sequence SEQ ID NO:1, its complement, DNA having the sequence SEQ ID NO:3 or its complement, under conditions comprising a) hybridization overnight in 5×Denhardt's solution, 5×SSC, 0.5% SDS and 2 mM EDTA at 68° C., b) washing twice with 2×SSC, 0.1% SDS for one hour at room temperature, and c) washing twice with 0.5×SSC, 0.1% SDS for one hour at 65°.

28. A nucleic acid vector comprising nucleic acid encoding a mycobacterial methionyl-tRNA synthetase of claim 27, wherein the mycobacterium is *Mycobacterium tuberculosis*.

29. A recombinant DNA vector comprising DNA which encodes a mycobacterial methionyl-tRNA synthetase.

30. A recombinant DNA vector comprising DNA which encodes a methionyl-tRNA synthetase of claim 29, wherein the mycobacterium is *Mycobacterium tuberculosis*.

31. A host cell comprising a recombinant nucleic acid which encodes an aminoacyl-tRNA synthetase of the genus Mycobacterium, wherein said aminoacyl-tRNA synthetase is selected from the group consisting of methionyl-tRNA synthetase, isoleucyl-tRNA synthetase, leucyl-tRNA synthetase, valyl-tRNA synthetase and cysteinyl-tRNA synthetase.

32. A host cell of claim 31, wherein the aminoacyl-tRNA synthetase is a leucyl-tRNA synthetase.

33. A host cell of claim 31, wherein the aminoacyl-tRNA synthetase is a valyl-tRNA synthetase.

34. A host cell of claim 31, wherein the aminoacyl-tRNA synthetase is a cysteinyl-tRNA synthetase.

35. A host cell comprising a recombinant nucleic acid, wherein said nucleic acid encodes a protein comprising a mycobacterial methionyl-tRNA synthetase.

36. A host cell of claim 35, wherein the mycobacterium is *Mycobacterium tuberculosis*.

37. A host cell comprising a recombinant nucleic acid, wherein said nucleic acid encodes a protein comprising a polypeptide having an amino acid sequence corresponding to amino acids 3–521 in SEQ ID NO:2.

38. A host cell which contains a recombinant mycobacterial methionyl-tRNA synthetase gene which can express a mycobacterial methionyl-tRNA synthetase.

39. A host cell of claim 38 in which the recombinant mycobacterial methionyl-tRNA synthetase gene is a *Mycobacterium tuberculosis* methionyl-tRNA synthetase gene.

40. An expression vector comprising a nucleic acid encoding a fusion protein comprising a mycobacterial aminoacyl-tRNA synthetase, wherein said aminoacyl-tRNA synthetase is selected from the group consisting of methionyl-tRNA synthetase, isoleucyl-tRNA synthetase, leucyl-tRNA synthetase, valyl-tRNA synthetase and cysteinyl-tRNA synthetase, and wherein the nucleic acid is under the control of transcriptional signals and is linked to appropriate translational signals for expression of said fusion protein in a suitable host cell.

41. An expression vector of claim 40, wherein the aminoacyl-tRNA synthetase is a methionyl-tRNA synthetase.

42. An expression vector of claim 41, wherein the mycobacterium is *Mycobacterium tuberculosis*.

43. A method for producing active mycobacterial methionyl-tRNA synthetase comprising the following steps:
   a) introducing a recombinant nucleic acid vector comprising a coding sequence for a mycobacterial methionyl-tRNA synthetase into suitable host cells; and
   b) maintaining the host cells under conditions suitable for expression.

44. A method for producing a mycobacterial aminoacyl-tRNA synthetase selected from the group consisting of methionyl-tRNA synthetase, isoleucyl-tRNA synthetase, leucyl-tRNA synthetase, valyl-tRNA synthetase and cysteinyl-tRNA synthetase, comprising maintaining a host cell comprising a recombinant nucleic acid encoding said mycobacterial aminoacyl-tRNA synthetase under conditions suitable for expression of the nucleic acid, whereby the encoded mycobacterial aminoacyl-tRNA synthetase is expressed and thereby produced.

45. The method of claim 44 further comprising the step of isolating the mycobacterial aminoacyl-tRNA synthetase.

46. The method of claim 44, wherein the aminoacyl-tRNA synthetase is a leucyl-tRNA synthetase.

47. The method of claim 44, wherein the aminoacyl-tRNA synthetase is a valyl-tRNA synthetase.

48. The method of claim 44, wherein the aminoacyl-tRNA synthetase is a cysteinyl-tRNA synthetase.

49. A method for producing a protein comprising a mycobacterial methionyl-tRNA synthetase, comprising maintaining a host cell comprising a recombinant nucleic acid encoding said protein under conditions suitable for expression of the nucleic acid, whereby the encoded protein is expressed and thereby produced,
   wherein said nucleic acid comprises a coding sequence for a mycobacterial methionyl-tRNA synthetase, and wherein said coding sequence hybridizes to DNA having the sequence SEQ ID NO:1, its complement, DNA having the sequence SEQ ID NO:3 or its complement, under conditions comprising a) hybridization overnight in 500 mM NaH$_2$PO$_4$(H$_2$O), 5% dextran sulfate, 7% SDS, 1 mM EDTA, 50% formamide, 250 mM NaCl, and 100 µg/ml salmon sperm DNA at 37° C., b) washing twice in 2×SSC, 0.1% SDS for 10 minutes each at room temperature, and c) washing twice in 0.5×SSC, 0.1% SDS for one hour each at 65°.

50. A method for producing a protein comprising a mycobacterial methionyl-tRNA synthetase, comprising maintaining a host cell comprising a recombinant nucleic acid encoding said protein under conditions suitable for expression of the nucleic acid, whereby the encoded protein is expressed and thereby produced,
   wherein said nucleic acid comprises a coding sequence for a mycobacterial methionyl-tRNA synthetase, and wherein said coding sequence hybridizes to DNA having the sequence SEQ ID NO:1, its complement, DNA having the sequence SEQ ID NO:3 or its complement, under conditions comprising a) hybridization overnight in 5×Denhardt's solution, 5×SSC, 0.5% SDS and 2 mM EDTA at 68° C., b) washing twice with 2×SSC, 0.1% SDS for one hour at room temperature, and c) washing twice with 0.5×SSC, 0.1% SDS for one hour at 65°.

51. A method for producing a protein comprising a methionyl-tRNA synthetase of a species of the genus Mycobacterium, comprising maintaining a host cell comprising a recombinant nucleic acid encoding said protein under conditions suitable for expression of the nucleic acid, whereby the encoded protein is expressed and thereby produced.

52. The method of claim 51 further comprising the step of isolating said protein.

53. A method for producing a protein comprising a methionyl-tRNA synthetase of *M. tuberculosis*, comprising maintaining a host cell containing a recombinant nucleic acid encoding said protein under conditions suitable for expression of the nucleic acid, whereby the encoded protein is expressed and thereby produced.

54. The method of claim 53 further comprising the step of isolating said protein.

55. An isolated nucleic acid comprising a nucleic acid which hybridizes to a DNA strand having the sequence shown in SEQ ID NO:1 or an RNA counterpart thereof under conditions comprising a) hybridization overnight in 500 mM NaH$_2$PO$_4$(H$_2$O), 5% dextran sulfate, 7% SDS, 1 MM EDTA, 50% formamide, 250 mM NaCl, and 100 µg/ml salmon sperm DNA at 37° C., b) washing twice in 2×SSC, 0.1% SDS for 10 minutes each at room temperature, and c) washing twice in 0.5×SSC, 0.1% SDS for one hour each at 65°.

56. An isolated nucleic acid, wherein said nucleic acid encodes a protein comprising a methionyl-tRNA synthetase which is encoded by pSH101A as deposited under ATCC Accession No. 98376.

57. The isolated nucleic acid of claim 56, wherein the protein is a fusion protein.

58. The isolated nucleic acid of claim 56, which is essentially pure.

59. A host cell comprising a recombinant nucleic acid, wherein said nucleic acid encodes a protein comprising a methionyl-tRNA synthetase which is encoded by pSH101A as deposited under ATCC Accession No. 98376.

60. A method for producing a protein comprising a methionyl-tRNA synthetase, comprising maintaining a host cell of claim 59 under conditions suitable for expression of said protein, whereby said protein is produced.

61. The method of claim 60 further comprising isolating said protein.

62. Plasmid pSH101A which is deposited in host cells under ATCC Accession No. 98376.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 2290 base pairs
        ( B ) TYPE: nucleic acid
        ( C ) STRANDEDNESS: double
        ( D ) TOPOLOGY: linear ( i i ) MOLECULE TYPE: other nucleic acid ( i x ) FEATURE:
        ( A ) NAME/KEY: CDS
        ( B ) LOCATION: 1..1563

( x i ) SEQUENCE DESCRIPTION: SEQ ID NO:1:

```
GTC GAA ATG AAG CCC TAT TAC GTC ACC ACC GCG ATC GCA TAT CCC AAC         48
Met Glu Met Lys Pro Tyr Tyr Val Thr Thr Ala Ile Ala Tyr Pro Asn
 1               5                  10                  15

GCT GCA CCC CAC GTA GGT CAC GCC TAC GAA TAC ATC GCC ACC GAC GCG         96
Ala Ala Pro His Val Gly His Ala Tyr Glu Tyr Ile Ala Thr Asp Ala
             20                  25                  30

ATC GCC CGG TTC AAA CGG CTG GAT GGC TAT GAC GTG CGC TTC CTG ACC        144
Ile Ala Arg Phe Lys Arg Leu Asp Gly Tyr Asp Val Arg Phe Leu Thr
         35                  40                  45

GGG ACC GAC GAG CAT GGC CTG AAG GTC GCA CAA GCC GCC GCG GCA GCG        192
Gly Thr Asp Glu His Gly Leu Lys Val Ala Gln Ala Ala Ala Ala Ala
     50                  55                  60

GGC GTG CCC ACC GCG GCG CTT GCC CGG CGC AAT TCC GAC GTG TTT CAG        240
Gly Val Pro Thr Ala Ala Leu Ala Arg Arg Asn Ser Asp Val Phe Gln
 65                  70                  75                  80

CGC ATG CAG GAG GCG CTG AAC ATC TCC TTC GAC CGA TTC ATC CGC ACT        288
Arg Met Gln Glu Ala Leu Asn Ile Ser Phe Asp Arg Phe Ile Arg Thr
                 85                  90                  95

ACC GAT GCC GAC CAC CAC GAG GCG TCC AAG GAA CTC TGG CGA CGG ATG        336
Thr Asp Ala Asp His His Glu Ala Ser Lys Glu Leu Trp Arg Arg Met
            100                 105                 110

TCG GCG GCC GGC GAC ATC TAT CTG GAC AAC TAT TCC GGG TGG TAC TCG        384
Ser Ala Ala Gly Asp Ile Tyr Leu Asp Asn Tyr Ser Gly Trp Tyr Ser
        115                 120                 125

GTG CGC GAC GAG CGG TTC TTC GTC GAA TCG GAG ACC CAA CTT GTC GAC        432
Val Arg Asp Glu Arg Phe Phe Val Glu Ser Glu Thr Gln Leu Val Asp
    130                 135                 140

GGC ACG CGC CTG ACG GTA GAG ACC GGC ACG CCG GTG ACC TGG ACC GAG        480
Gly Thr Arg Leu Thr Val Glu Thr Gly Thr Pro Val Thr Trp Thr Glu
145                 150                 155                 160

GAG CAG ACC TAC TTC TTC CGG CTG TCG GCC TAT ACC GAC AAG CTG CTG        528
Glu Gln Thr Tyr Phe Phe Arg Leu Ser Ala Tyr Thr Asp Lys Leu Leu
                165                 170                 175

GCC CAC TAT CAC GCC AAC CCC GAC TTC ATC GCG CCG GAG ACG CGG CGC        576
Ala His Tyr His Ala Asn Pro Asp Phe Ile Ala Pro Glu Thr Arg Arg
            180                 185                 190

AAC GAA GTG ATC AGC TTC GTC TCC GGC GGC CTG GAC GAC CTG TCG ATC        624
Asn Glu Val Ile Ser Phe Val Ser Gly Gly Leu Asp Asp Leu Ser Ile
        195                 200                 205

TCG CGC ACC TCG TTT GAC TGG GGT GTG CAG GTG CCC GAG CAC CCC GAC        672
Ser Arg Thr Ser Phe Asp Trp Gly Val Gln Val Pro Glu His Pro Asp
    210                 215                 220
```

| | | | | | | | | | | | | | | | | |
|---|---|---|---|---|---|---|---|---|---|---|---|---|---|---|---|---|
| CAC | GTC | ATG | TAC | GTC | TGG | GTC | GTC | GCG | CTG | ACC | AAT | TAC | CTG | ACC | GGG | 720 |
| His | Val | Met | Tyr | Val | Trp | Val | Val | Ala | Leu | Thr | Asn | Tyr | Leu | Thr | Gly | |
| 225 | | | | 230 | | | | | 235 | | | | | 240 | | |
| GCG | GGC | TTC | CCG | GAT | ACC | GAC | TCG | GAG | TTG | TTC | CGC | CGC | TAC | TGG | CCC | 768 |
| Ala | Gly | Phe | Pro | Asp | Thr | Asp | Ser | Glu | Leu | Phe | Arg | Arg | Tyr | Trp | Pro | |
| | | | 245 | | | | | 250 | | | | | 255 | | | |
| GCC | GAT | TTG | CAC | ATG | ATC | GCG | AAG | GAC | ATC | ATC | AGG | TTT | CAT | GCC | GTC | 816 |
| Ala | Asp | Leu | His | Met | Ile | Ala | Lys | Asp | Ile | Ile | Arg | Phe | His | Ala | Val | |
| | | | 260 | | | | 265 | | | | | 270 | | | | |
| TAT | TGG | CCG | GCG | TTT | TTG | ATG | TCA | GCC | GGA | ATC | GAG | TTG | CCG | CGA | AGG | 864 |
| Tyr | Trp | Pro | Ala | Phe | Leu | Met | Ser | Ala | Gly | Ile | Glu | Leu | Pro | Arg | Arg | |
| | | 275 | | | | 280 | | | | | 285 | | | | | |
| ATC | TTC | GCG | CAC | GGG | TTC | TTG | CAC | AAC | CGC | GGC | GAG | AAG | ATG | AGT | AAA | 912 |
| Ile | Phe | Ala | His | Gly | Phe | Leu | His | Asn | Arg | Gly | Glu | Lys | Met | Ser | Lys | |
| | | 290 | | | | 295 | | | | | 300 | | | | | |
| TCG | GTG | GGC | AAC | ATC | GTC | GAC | CCG | GTT | GCC | CTG | GCG | GAA | GCG | CTC | GGG | 960 |
| Ser | Val | Gly | Asn | Ile | Val | Asp | Pro | Val | Ala | Leu | Ala | Glu | Ala | Leu | Gly | |
| 305 | | | | 310 | | | | | 315 | | | | | 320 | | |
| GTG | GAC | CAG | GTC | CGC | TAC | TTC | CTG | TTG | CGG | GAG | GTC | CCG | TTC | GGC | CAG | 1008 |
| Val | Asp | Gln | Val | Arg | Tyr | Phe | Leu | Leu | Arg | Glu | Val | Pro | Phe | Gly | Gln | |
| | | | | 325 | | | | | 330 | | | | | 335 | | |
| GAC | GGC | AGT | TAC | AGC | GAC | GAG | GCC | ATC | GTC | ACT | CGG | ATC | AAC | ACC | GAT | 1056 |
| Asp | Gly | Ser | Tyr | Ser | Asp | Glu | Ala | Ile | Val | Thr | Arg | Ile | Asn | Thr | Asp | |
| | | | 340 | | | | | 345 | | | | | 350 | | | |
| CTG | GCC | AAC | GAG | CTC | GGC | AAC | TTG | GCC | CGG | CGC | TCG | TTG | TCG | ATG | GTG | 1104 |
| Leu | Ala | Asn | Glu | Leu | Gly | Asn | Leu | Ala | Arg | Arg | Ser | Leu | Ser | Met | Val | |
| | | | 355 | | | | | 360 | | | | | 365 | | | |
| GCC | AAA | AAC | CTT | GAC | GGC | AGG | GTG | CCC | AAC | CCG | GGT | GAG | TTC | GCC | GAC | 1152 |
| Ala | Lys | Asn | Leu | Asp | Gly | Arg | Val | Pro | Asn | Pro | Gly | Glu | Phe | Ala | Asp | |
| | 370 | | | | | 375 | | | | | 380 | | | | | |
| GCC | GAC | GCC | GCG | CTG | CTT | GCG | ACC | GCC | GAT | GGC | TTG | TTG | GAG | CGA | GTG | 1200 |
| Ala | Asp | Ala | Ala | Leu | Leu | Ala | Thr | Ala | Asp | Gly | Leu | Leu | Glu | Arg | Val | |
| 385 | | | | | 390 | | | | | 395 | | | | | 400 | |
| CGC | GGT | CAC | TTC | GAC | GCA | CAG | GCG | ATG | CAC | CTG | GCG | CTG | GAG | GCG | ATC | 1248 |
| Arg | Gly | His | Phe | Asp | Ala | Gln | Ala | Met | His | Leu | Ala | Leu | Glu | Ala | Ile | |
| | | | | 405 | | | | | 410 | | | | | 415 | | |
| TGG | CTG | ATG | CTC | GGC | GAC | GCG | AAC | AAG | TAC | TTT | TCG | GTG | CAG | CAG | CCG | 1296 |
| Trp | Leu | Met | Leu | Gly | Asp | Ala | Asn | Lys | Tyr | Phe | Ser | Val | Gln | Gln | Pro | |
| | | | 420 | | | | | 425 | | | | | 430 | | | |
| TGG | GTA | CTG | CGC | AAG | AGC | GAG | TCC | GAA | GCC | GAT | CAG | GCC | CGG | TTC | CGC | 1344 |
| Trp | Val | Leu | Arg | Lys | Ser | Glu | Ser | Glu | Ala | Asp | Gln | Ala | Arg | Phe | Arg | |
| | | 435 | | | | | 440 | | | | | 445 | | | | |
| ACC | ACG | CTC | TAC | GTC | ACC | TGC | GAG | GTA | GTC | CGC | ATC | GCG | GCA | CTG | CTG | 1392 |
| Thr | Thr | Leu | Tyr | Val | Thr | Cys | Glu | Val | Val | Arg | Ile | Ala | Ala | Leu | Leu | |
| | 450 | | | | | 455 | | | | | 460 | | | | | |
| ATC | CAG | CCG | GTG | ATG | CCG | GAG | TCG | GCC | GGC | AAA | ATT | TTG | GAC | CTG | CTC | 1440 |
| Ile | Gln | Pro | Val | Met | Pro | Glu | Ser | Ala | Gly | Lys | Ile | Leu | Asp | Leu | Leu | |
| 465 | | | | | 470 | | | | | 475 | | | | | 480 | |
| GGC | CAG | GCC | CCA | AAC | CAG | CGG | TCG | TTC | GCC | GCC | GTA | GGT | GTT | CGG | CTG | 1488 |
| Gly | Gln | Ala | Pro | Asn | Gln | Arg | Ser | Phe | Ala | Ala | Val | Gly | Val | Arg | Leu | |
| | | | | 485 | | | | | 490 | | | | | 495 | | |
| ACC | CCC | GGC | ACA | GCG | CTG | CCG | CCG | CCC | ACC | GGG | GTA | TTT | CCC | CGC | TAC | 1536 |
| Thr | Pro | Gly | Thr | Ala | Leu | Pro | Pro | Pro | Thr | Gly | Val | Phe | Pro | Arg | Tyr | |
| | | | 500 | | | | | 505 | | | | | 510 | | | |
| CAG | CCG | CCG | CAA | CCA | CCC | GAA | GGC | AAG | TGAGCGGACC | | GCAGCGACGG | | | | | 1583 |
| Gln | Pro | Pro | Gln | Pro | Pro | Glu | Gly | Lys | | | | | | | | |
| | | 515 | | | | | 520 | | | | | | | | | |
| GAAAGCCACC | TACGAAGCGT | TGACCGCGGT | CTGCGCGTCG | CGTGGGATGT | CGAGCGTGGC | | | | | | | | | | | 1643 |
| GACGGGATAA | AACCCGGAAT | CGTCGCGGCC | GTCGCGGGAC | AACAGCATGG | GCGGATAGTT | | | | | | | | | | | 1703 |

```
CACCACATGG GAGCCGTTCG GTTTGTGCTG TTGCCAGTCG ATCGCGGCCC GCAGCGTGTA    1763

GTGGCCCGCG GGCAAGCCGG ACAGATCAAC GCGAACCGTC TCGGCGACCG ACGCCGGTGT    1823

CGGCTGGTCG CTGCTGCGAT CGCCGCGCTG GTCGGAGACC AGCGTCTTCA GGTCCACCGC    1883

TGCCGGCAGC GTCCGAACCA CCTGTCCGGT GGAATCCACC AGCCGGTAGC CGGGCACCCA    1943

CTTTTCGGTG GCGGCAGCAG CGCCGTAGTT GGTCCAGGTG ACCGAGATCG TCGCGACCTT    2003

GCCCGCTAGC GCTTGCGACC CCGGCTGCGC TTCGACCGAG TACCGATAGC CTGCGGCGGC    2063

GTTAGCTTGC GCCCACACCA GGTACAACGC GGGGTCCATC GGCGAGGTCG CCGTCTGGTC    2123

GGGGAAGTTA ACGCTCGACG TCATCGACAC GTGATACCTG ATGACGTCGC GCAGGCCCTT    2183

CTCGTAGTAA GCCCGCGGCG AACTGCCGGT CGGCAACTCG CACCACTCGG TGATCACCGG    2243

CGCCGTTGCC AGCCGCTGCC GCAGCGCGCG ACCACCGGGT CTTTGGT                  2290
```

( 2 ) INFORMATION FOR SEQ ID NO:2:

( i ) SEQUENCE CHARACTERISTICS:
        ( A ) LENGTH: 521 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Met Lys Pro Tyr Tyr Val Thr Thr Ala Ile Ala Tyr Pro Asn
 1               5                  10                  15

Ala Ala Pro His Val Gly His Ala Tyr Glu Tyr Ile Ala Thr Asp Ala
             20                  25                  30

Ile Ala Arg Phe Lys Arg Leu Asp Gly Tyr Asp Val Arg Phe Leu Thr
         35                  40                  45

Gly Thr Asp Glu His Gly Leu Lys Val Ala Gln Ala Ala Ala Ala Ala
     50                  55                  60

Gly Val Pro Thr Ala Ala Leu Ala Arg Arg Asn Ser Asp Val Phe Gln
 65                  70                  75                  80

Arg Met Gln Glu Ala Leu Asn Ile Ser Phe Asp Arg Phe Ile Arg Thr
                 85                  90                  95

Thr Asp Ala Asp His His Glu Ala Ser Lys Glu Leu Trp Arg Arg Met
            100                 105                 110

Ser Ala Ala Gly Asp Ile Tyr Leu Asp Asn Tyr Ser Gly Trp Tyr Ser
        115                 120                 125

Val Arg Asp Glu Arg Phe Phe Val Glu Ser Glu Thr Gln Leu Val Asp
    130                 135                 140

Gly Thr Arg Leu Thr Val Glu Thr Gly Thr Pro Val Thr Trp Thr Glu
145                 150                 155                 160

Glu Gln Thr Tyr Phe Phe Arg Leu Ser Ala Tyr Thr Asp Lys Leu Leu
                165                 170                 175

Ala His Tyr His Ala Asn Pro Asp Phe Ile Ala Pro Glu Thr Arg Arg
            180                 185                 190

Asn Glu Val Ile Ser Phe Val Ser Gly Gly Leu Asp Asp Leu Ser Ile
        195                 200                 205

Ser Arg Thr Ser Phe Asp Trp Gly Val Gln Val Pro Glu His Pro Asp
    210                 215                 220

His Val Met Tyr Val Trp Val Val Ala Leu Thr Asn Tyr Leu Thr Gly
225                 230                 235                 240

Ala Gly Phe Pro Asp Thr Asp Ser Glu Leu Phe Arg Arg Tyr Trp Pro
                245                 250                 255
```

| | | | | | | | | | | | | | | |
|---|---|---|---|---|---|---|---|---|---|---|---|---|---|---|
|Ala|Asp|Leu|His 260|Met|Ile|Ala|Lys|Asp 265|Ile|Ile|Arg|Phe|His 270|Ala|Val|
|Tyr|Trp|Pro 275|Ala|Phe|Leu|Met|Ser 280|Ala|Gly|Ile|Glu|Leu 285|Pro|Arg|Arg|
|Ile|Phe 290|Ala|His|Gly|Phe|Leu 295|His|Asn|Arg|Gly|Glu 300|Lys|Met|Ser|Lys|
|Ser 305|Val|Gly|Asn|Ile|Val 310|Asp|Pro|Val|Ala|Leu 315|Ala|Glu|Ala|Leu|Gly 320|
|Val|Asp|Gln|Val|Arg 325|Tyr|Phe|Leu|Leu|Arg 330|Glu|Val|Pro|Phe|Gly 335|Gln|
|Asp|Gly|Ser|Tyr 340|Ser|Asp|Glu|Ala|Ile 345|Val|Thr|Arg|Ile|Asn 350|Thr|Asp|
|Leu|Ala|Asn 355|Glu|Leu|Gly|Asn|Leu 360|Ala|Arg|Arg|Ser|Leu 365|Ser|Met|Val|
|Ala|Lys 370|Asn|Leu|Asp|Gly|Arg 375|Val|Pro|Asn|Pro|Gly 380|Glu|Phe|Ala|Asp|
|Ala 385|Asp|Ala|Ala|Leu|Leu 390|Ala|Thr|Ala|Asp|Gly 395|Leu|Leu|Glu|Arg|Val 400|
|Arg|Gly|His|Phe|Asp 405|Ala|Gln|Ala|Met|His 410|Leu|Ala|Leu|Glu|Ala 415|Ile|
|Trp|Leu|Met|Leu 420|Gly|Asp|Ala|Asn|Lys 425|Tyr|Phe|Ser|Val|Gln 430|Gln|Pro|
|Trp|Val|Leu 435|Arg|Lys|Ser|Glu|Ser 440|Glu|Ala|Asp|Gln|Ala 445|Arg|Phe|Arg|
|Thr|Thr 450|Leu|Tyr|Val|Thr|Cys 455|Glu|Val|Val|Arg|Ile 460|Ala|Ala|Leu|Leu|
|Ile 465|Gln|Pro|Val|Met|Pro 470|Glu|Ser|Ala|Gly|Lys 475|Ile|Leu|Asp|Leu|Leu 480|
|Gly|Gln|Ala|Pro|Asn 485|Gln|Arg|Ser|Phe|Ala 490|Ala|Val|Gly|Val|Arg 495|Leu|
|Thr|Pro|Gly|Thr 500|Ala|Leu|Pro|Pro|Thr 505|Gly|Val|Phe|Pro 510|Arg|Tyr| |
|Gln|Pro|Pro 515|Gln|Pro|Pro|Glu|Gly 520|Lys| | | | | | | |

(2) INFORMATION FOR SEQ ID NO:3:

( i ) SEQUENCE CHARACTERISTICS:
        ( A ) LENGTH: 599 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

| | | | | | |
|---|---|---|---|---|---|
|GCGAATTCGT|AGCCGATGGT|GGCGTCGAGC|CAGACGTACA|TGACGTGGTC|CGGATGCTCC|60|
|GGCACAGGCA|CGCCCCAGTT|GAACGACGTC|CGCGACACCG|ACAGGTGTTT|GCGGCCGCCG|120|
|GACACGAAGC|TGATCACCTC|GTTACGCCGT|ACCTCGGGTG|CGATGAAGTC|GGGGTGGGCG|180|
|TGGTAGTGGG|CCAGCAGCTT|GTCGGCGTAG|GCAGCCGGAA|GAAGTAGGTC|TGCTCCTCGG|240|
|TCCAGGTCAC|CGGGGTGCCG|GTCTCGATGG|CGATCCGGGT|GCCGTCGACG|AGTTGGGTCT|300|
|CCGACTCGAC|GAAAAACCGC|TCGTCGCGCA|CCGAGTACCA|GCCGGAGTAG|TTGTCCAGGT|360|
|AGAGATCACC|GGCGGCCTCC|ATCCGGCGCC|AGATCTCCTG|CGACGCCGCG|TAGTGGTCGG|420|
|GGTCGGTGGT|GCGGATGAAC|CGGTCGAAGG|AGATGTTCAG|CGCCTCCTGC|ATGCGCTGGA|480|

| | | | | | |
|---|---|---|---|---|---|
| AGACGTCGGA | ATTGCGCCGG | GCAAGCTGTG | CGGTCGGCAC | GCCCGCGGCC | GCGGCGGCCT | 540 |
| GCGCCACCTT | CAGGCCGTGC | TCATCCGTCC | CCGTCAGATA | GAATTCGCGG | GGATCCTCT | 599 |

( 2 ) INFORMATION FOR SEQ ID NO:4:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:4:

| | | | |
|---|---|---|---|
| CCGGAATTCT | TAACGATTCC | GGGTTTTATC | CCGTCGCCAC | 40 |

( 2 ) INFORMATION FOR SEQ ID NO:5:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:5:

| | | | |
|---|---|---|---|
| CCGGATCCCG | TACGATTCCG | GGTTTTATCC | CGTCGCCAC | 39 |

( 2 ) INFORMATION FOR SEQ ID NO:6:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:6:

| | | | | |
|---|---|---|---|---|
| GCGCTCTAGA | TATCTGCTTA | TGTCCCTAT | ACTAGGTTAT | TGG | 43 |

( 2 ) INFORMATION FOR SEQ ID NO:7:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:7:

| | | |
|---|---|---|
| GGGGTACCTC | ACGATGCGGC | CGCTCGAG | 28 |

( 2 ) INFORMATION FOR SEQ ID NO:8:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:8:

| | | | |
|---|---|---|---|
| CCGCTCGAGC | GATGCAATGT | CGATCAATTG | TGC | 33 |

( 2 ) INFORMATION FOR SEQ ID NO:9:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:9:

```
GGGGTACCCC TTTTTCATGA CCTCATATTC G                                    31
```

( 2 ) INFORMATION FOR SEQ ID NO:10:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( i x ) FEATURE:
        ( A ) NAME/KEY: modified_base
        ( B ) LOCATION: 14
        ( D ) OTHER INFORMATION: /mod_base=i ( i x ) FEATURE:
        ( A ) NAME/KEY: modified_base
        ( B ) LOCATION: 17
        ( D ) OTHER INFORMATION: /mod_base=i ( i x ) FEATURE:
        ( A ) NAME/KEY: modified_base
        ( B ) LOCATION: 20
        ( D ) OTHER INFORMATION: /mod_base=i ( i x ) FEATURE:
        ( A ) NAME/KEY: modified_base
        ( B ) LOCATION: 23
        ( D ) OTHER INFORMATION: /mod_base=i ( x i ) SEQUENCE DESCRIPTION: SEQ ID NO:10:

```
GCGAATTCTW YCTNACNGGN ACNGAYGARC AYGG                                 34
```

( 2 ) INFORMATION FOR SEQ ID NO:11:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( i x ) FEATURE:
        ( A ) NAME/KEY: modified_base
        ( B ) LOCATION: 14
        ( D ) OTHER INFORMATION: /mod_base=i ( i x ) FEATURE:
        ( A ) NAME/KEY: modified_base
        ( B ) LOCATION: 20
        ( D ) OTHER INFORMATION: /mod_base=i ( i x ) FEATURE:
        ( A ) NAME/KEY: modified_base
        ( B ) LOCATION: 23
        ( D ) OTHER INFORMATION: /mod_base=i ( x i ) SEQUENCE DESCRIPTION: SEQ ID NO:11:

```
GCGAATTCTT YATNTGYGGN ACNGAYGARY AYGG                                 34
```

( 2 ) INFORMATION FOR SEQ ID NO:12:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: other nucleic acid ( i x ) FEATURE:
    ( A ) NAME/KEY: modified_base
    ( B ) LOCATION: 15
    ( D ) OTHER INFORMATION: /mod_base=i ( i x ) FEATURE:
    ( A ) NAME/KEY: modified_base
    ( B ) LOCATION: 18
    ( D ) OTHER INFORMATION: /mod_base=i ( i x ) FEATURE:
    ( A ) NAME/KEY: modified_base
    ( B ) LOCATION: 21
    ( D ) OTHER INFORMATION: /mod_base=i ( i x ) FEATURE:
    ( A ) NAME/KEY: modified_base
    ( B ) LOCATION: 33
    ( D ) OTHER INFORMATION: /mod_base=i ( x i ) SEQUENCE DESCRIPTION: SEQ ID NO:12:

GCGAATTCRT ARTTNATNAG NGCRTCRAWC CANACRTA                    38

( 2 ) INFORMATION FOR SEQ ID NO:13:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: other nucleic acid ( i x ) FEATURE:
    ( A ) NAME/KEY: modified_base
    ( B ) LOCATION: 12
    ( D ) OTHER INFORMATION: /mod_base=i ( i x ) FEATURE:
    ( A ) NAME/KEY: modified_base
    ( B ) LOCATION: 18
    ( D ) OTHER INFORMATION: /mod_base=i ( i x ) FEATURE:
    ( A ) NAME/KEY: modified_base
    ( B ) LOCATION: 21
    ( D ) OTHER INFORMATION: /mod_base=i ( i x ) FEATURE:
    ( A ) NAME/KEY: modified_base
    ( B ) LOCATION: 27
    ( D ) OTHER INFORMATION: /mod_base=i ( i x ) FEATURE:
    ( A ) NAME/KEY: modified_base
    ( B ) LOCATION: 33
    ( D ) OTHER INFORMATION: /mod_base=i ( x i ) SEQUENCE DESCRIPTION: SEQ ID NO:13:

GCGAATTCRT ANCCRATNGK NGCRTCNARC CANACRTA                    38

( 2 ) INFORMATION FOR SEQ ID NO:14:

( i ) SEQUENCE CHARACTERISTICS:
    ( A ) LENGTH: 9 amino acids
    ( B ) TYPE: amino acid ( C ) STRANDEDNESS:
( D ) TOPOLOGY: linear ( i i ) MOLECULE TYPE: peptide ( x i ) SEQUENCE DESCRIPTION: SEQ ID NO:14:

Phe Leu Thr Gly Thr Asp Glu His Gly
 1               5

( 2 ) INFORMATION FOR SEQ ID NO:15:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:15:

Tyr Leu Thr Gly Thr Asp Glu His Gly
 1               5

( 2 ) INFORMATION FOR SEQ ID NO:16:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:16:

Phe Thr Thr Gly Thr Asp Glu His Gly
 1               5

( 2 ) INFORMATION FOR SEQ ID NO:17:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:17:

Phe Ile Cys Ala Asp Asp Ala His Gly
 1               5

( 2 ) INFORMATION FOR SEQ ID NO:18:

( i ) SEQUENCE CHARACTERISTICS:
( A ) LENGTH: 9 amino acids
( B ) TYPE: amino acid
( C ) STRANDEDNESS:
( D ) TOPOLOGY: linear ( i i ) MOLECULE TYPE: peptide ( x i ) SEQUENCE DESCRIPTION: SEQ ID NO:18:

Phe Ile Cys Gly Thr Asp Glu Tyr Gly
 1               5

( 2 ) INFORMATION FOR SEQ ID NO:19:

( i ) SEQUENCE CHARACTERISTICS:
( A ) LENGTH: 10 amino acids
( B ) TYPE: amino acid

```
            ( C ) STRANDEDNESS:
            ( D ) TOPOLOGY: linear ( i i ) MOLECULE TYPE: peptide ( x i ) SEQUENCE DESCRIPTION: SEQ ID NO:19:

Tyr  Val  Trp  Phe  Asp  Ala  Leu  Leu  Asn  Tyr
        1                   5                        10

( 2 ) INFORMATION FOR SEQ ID NO:20:

( i ) SEQUENCE CHARACTERISTICS:
            ( A ) LENGTH: 10 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:20:

Tyr  Val  Trp  Ile  Asp  Ala  Leu  Ala  Asn  Tyr
        1                   5                        10

( 2 ) INFORMATION FOR SEQ ID NO:21:

( i ) SEQUENCE CHARACTERISTICS:
            ( A ) LENGTH: 10 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:21:

Tyr  Val  Trp  Phe  Asp  Ala  Leu  Cys  Asn  Tyr
        1                   5                        10

( 2 ) INFORMATION FOR SEQ ID NO:22:

( i ) SEQUENCE CHARACTERISTICS:
            ( A ) LENGTH: 10 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:22:

Tyr  Val  Trp  Leu  Asp  Ala  Pro  Ile  Gly  Tyr
        1                   5                        10

( 2 ) INFORMATION FOR SEQ ID NO:23:

( i ) SEQUENCE CHARACTERISTICS:
            ( A ) LENGTH: 10 amino acids
            ( B ) TYPE: amino acid
            ( C ) STRANDEDNESS:
            ( D ) TOPOLOGY: linear ( i i ) MOLECULE TYPE: peptide ( x i ) SEQUENCE DESCRIPTION: SEQ ID NO:23:

Tyr  Val  Trp  Phe  Asp  Ala  Thr  Ile  Gly  Tyr
        1                   5                        10
```